(12) United States Patent
Uckun

(10) Patent No.: US 7,144,874 B2
(45) Date of Patent: Dec. 5, 2006

(54) ARYL PHOSPHATE DERIVATIVES OF D4T HAVING ACTIVITY AGAINST RESISTANT HIV STRAINS

(75) Inventor: Fatih M. Uckun, White Bear Lake, MN (US)

(73) Assignee: Parker Hughes Institute, Roseville, MN (US)

( * ) Notice: Subject to any disclaimer, the term of this patent is extended or adjusted under 35 U.S.C. 154(b) by 369 days.

(21) Appl. No.: 10/281,333

(22) Filed: Oct. 25, 2002

(65) Prior Publication Data

US 2004/0087549 A1 May 6, 2004

(51) Int. Cl.
*A61K 31/70* (2006.01)
(52) U.S. Cl. ............ 514/51; 514/26.1; 514/26.6; 514/26.8; 514/28.2; 514/49; 514/50; 514/885
(58) Field of Classification Search ............ 514/51, 514/49, 50, 885, 26.1, 26.6, 26.8, 28.2
See application file for complete search history.

(56) References Cited

U.S. PATENT DOCUMENTS

| | | | |
|---|---|---|---|
| 4,841,039 A | 6/1989 | Chu et al. | |
| 6,030,957 A | 2/2000 | Uckun et al. | |
| 6,350,736 B1 * | 2/2002 | Uckun et al. | 514/51 |
| 6,670,336 B1 * | 12/2003 | Uckun et al. | 514/51 |

OTHER PUBLICATIONS

Erice, A. et al., "Anti-Human Immunodeficiency Virus Type 1 Activity of an Anti-CD4 Immunoconjugate Containing Pokeweed Antiviral Protein," *Antimicrobial Agents and Chemotherapy*, vol. 37, No. 4, pp. 835-838 (Apr. 1993).
Gottlieb, M. "AIDS—Past and Future," *N. Engl. J. Med.*, vol. 344, No. 23, pp. 17881791 (Jun. 7, 2001).
Hu, D. et al., "The Emerging Genetic Diversity of HIV—The Importance of Global Surveillance for Diagnostics, Research, and Prevention," *JAMA*, vol. 275, No. 3, pp. 210-216 (Jan. 17, 1996).
Mansuri, M. et al., "1-(2,3-Dideoxy-β-D-glycero-pent-2-enofuranosyl)thymine. A Highly Potent and Selective Anti-HIV Agent," *J. Med. Chem.*, vol. 32, No. 2, pp. 461-466 (Feb. 1989).
McGuigan, C. et al., "Aryl phosphate derivatives of AZT retain activity against HIV1 in cell lines which are resistant to the action of AZT," *Antiviral Research*, vol. 17, pp. 311-321 (1992).

McGuigan, C. et al., "Phosphoramidate Derivatives of d4T with Improved Anti-HIV Efficacy Retain Full Activity in Thymidine Kinase-Deficient Cells," *Bioorganic & Medicinal Chemistry Letters*, vol. 6, No. 10, pp. 1183-1186 (May 21, 1996).
McIntee, E. et al., "Probing the Mechanism of Action and Decomposition of Amino Acid Phosphomonoester Amidates of Antiviral Nucleoside Prodrugs," *J. Med. Chem.*, vol. 40, No. 21, pp. 3323-3331 (Oct. 10, 1997).
Richman, D., "HIV Chemotherapy," *Nature*, vol. 410, pp. 995-1001 (Apr. 19, 2001).
Richman et al., "In Vitro Evaluation of Experimental Agents for Anti-HIV Activty," *Current Protocols in Immunology*, vol. 3, Supplement 8, Unit 12.9, pp. 1-21 (1993).
Sepkowitz, K., "AIDS—The First 20 Years," *N. Engl. J. Med.*, vol. 344, No. 23, pp. 1764-1772 (Jun. 7, 2001).
Shafer, R. et al., "A Guide to HIV-1 Reverse Transcriptase and Protease Sequencing for Drug Resistance Studies," pp. 1-51 (2001).
Siddiqui, A. et al., "Design and Synthesis of Lipophilic Phosphoramidate d4T-MP Prodrugs Expressing High Potency Against HIV in Cell Culture: Structural Determinants for in Vitro Activity and QSAR," *J. Med. Chem.*, vol. 42, No. 20, pp. 4122-4128 (1999).
Uckun, F. et al., "TXU (Anti-CD7)-Pokeweed Antiviral Protein as a Potent Inhibitor of Human Immunodeficiency Virus," *Antimicrobial Agents and Chemotherapy*, vol. 42, No. 2, pp. 383-388 (Feb. 1998).
Venkatachalam, T. et al., "Enhancing Effects of a Mono-Bromo Substitution at the PARA Position of the Phenyl Moiety on the Metabolism and Anti-HIV Activity of D4T-Phenyl Methoxyalaninyl Phosphate Derivatives," *Biog. & Mech. Chem. Letters*, vol. 8, No. 22, pp. 3121-3126 (Nov. 17, 1998).
Vig, R. et al., "D4T-5'-[p-Bromophenyl methoxyalaninyl phosphate] as a potent and non-toxic anti-human immunodeficiency virus agent," *Antiviral Chemistry & Chemotherapy*, vol. 9, pp. 445-428 (1998).
Zarling, J. et al., "Inhibition of HIV replication by pokeweed antiviral protein targeted to $CD4^+$ cells by monoclonal antibodies," *Letters to Nature*, vol. 347, No. 6288, pp. 92-95 (Sep. 6, 1990).

* cited by examiner

*Primary Examiner*—Sreeni Padmanabhan
*Assistant Examiner*—Jennifer Kim
(74) *Attorney, Agent, or Firm*—Merchant & Gould P.C.

(57) ABSTRACT

Methods of inhibiting virus replication of in a cell infected with a resistant strain of HIV that includes administering to the infected cell a virus replication inhibiting amount of an aryl phosphate derivative of d4T.

15 Claims, 7 Drawing Sheets

Figure 2A
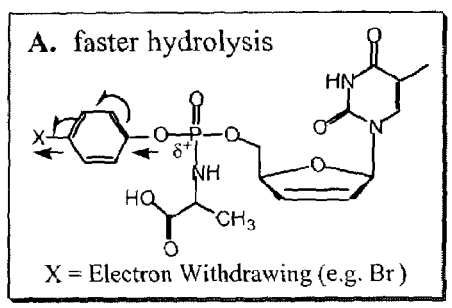
Figure 2B
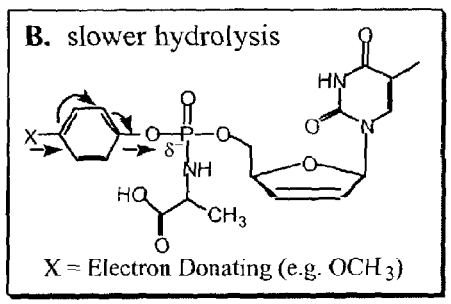
Figure 2C
Figure 2D
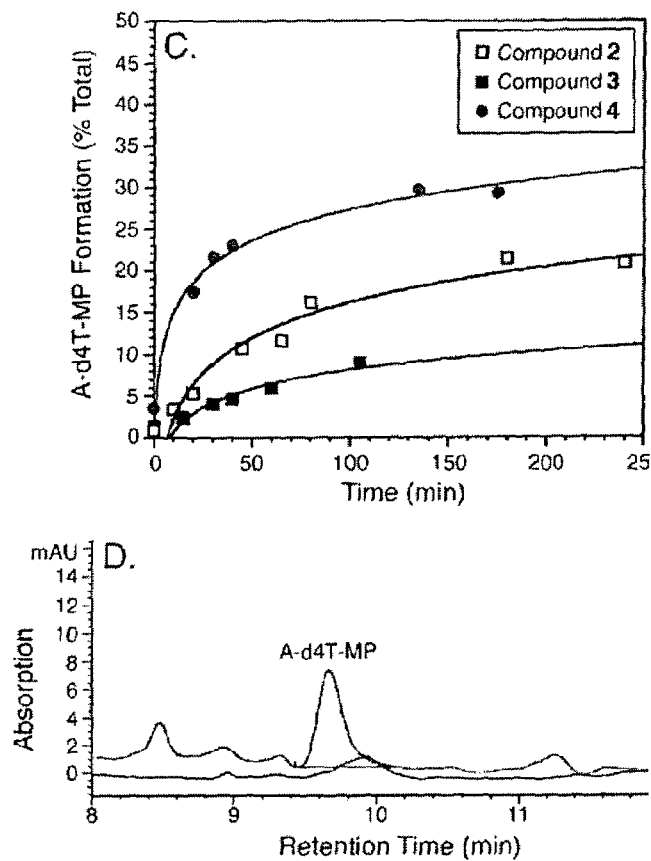

A

B

ARYL PHOSPHATE DERIVATIVES OF D4T HAVING ACTIVITY AGAINST RESISTANT HIV STRAINS

BACKGROUND OF THE INVENTION

According to recent estimates, 36.1 million persons worldwide are infected with human immunodeficiency virus ("HIV") (Gottlieb M S, 2001 *N Engl J Med* 344(23): 1788–91 and Sepkowitz K A. 2001 N Engl J Med 344(23): 1764–72). There are currently a number of anti-retroviral drugs available for clinical use, and these have lead to significant reductions in morbidity and mortality for HIV-infected individuals. Contemporary treatment of HIV infected patients in the United States is generally combination antiretroviral therapy with at least two of three classes of antiretroviral therapy: nucleoside analog reverse transcriptase (RT) inhibitors (NRTI), non-nucleoside analog RT inhibitors (NNRTI), and protease inhibitors. The individual agents in the combination therapy can select for drug-resistant strains and thereby create a reservoir of multidrug resistant HIV that can limit future treatment options.

Currently available anti-HIV agents have been developed against subtype B HIV-1 strains, the predominant HIV strains in the USA and Europe. However, the majority of HIV-infected individuals worldwide are infected with non-subtype B strains, and the majority of new infections worldwide, including the USA and Europe, are caused by non-subtype B strains (Hu et al. 1996 *JAMA* 275: 210–6; Richman D D et al., In: *Current Protocols in Immunology*, John Wiley & Sons, Inc., Brooklyn, N.Y., Suppl 8, Unit 12.9, pp. 1–21, 1993). These non-subtype B strains are generally unaffected by commonly used anti-HIV treatment protocols.

Therefore, there is a need to identify potent and effective anti-HIV agents that have activity against resistant strains, including known drug resistant strains and non-subtype B strains of HIV.

SUMMARY OF THE INVENTION

The invention provides methods of inhibiting virus replication in a cell infected with a resistant strain of HIV comprising administering to the infected cell a virus replication inhibiting amount of a compound of Formula I

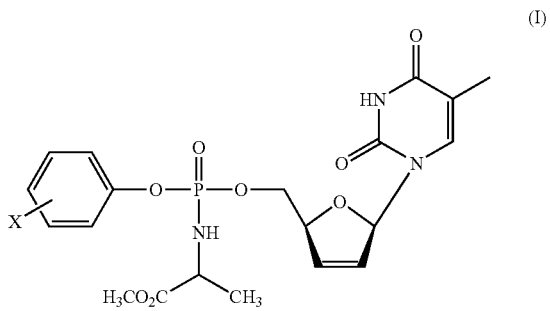

(I)

wherein X is an electron withdrawing group, and $R_2$ is an amino acid residue.

The invention also offers methods of treating a patient infected with a resistant strain of HIV and or non-subtype B strain of HIV comprising administering to the patient a therapeutically effective amount of a compound of Formula I.

BRIEF DESCRIPTION OF THE DRAWINGS

FIGS. 2A and 2B are diagrams showing the electron withdrawing hypothesis for the enhanced hydrolysis of a substituted phenyl ring.

FIG. 2C is an elution profile showing production of A-d4T as a result of hydrolysis of each of the tested compounds: Compound 2, where X=H (open squares); Compound 3, where X=$OCH_3$ (filled squares); and Compound 4, where X=Br (filled circles).

FIG. 2D is an elution profile showing the sensitivity of the tested compounds to enzymatic hydrolysis by porcine liver esterase.

DETAILED DESCRIPTION OF THE INVENTION

Definitions

Figure 1:
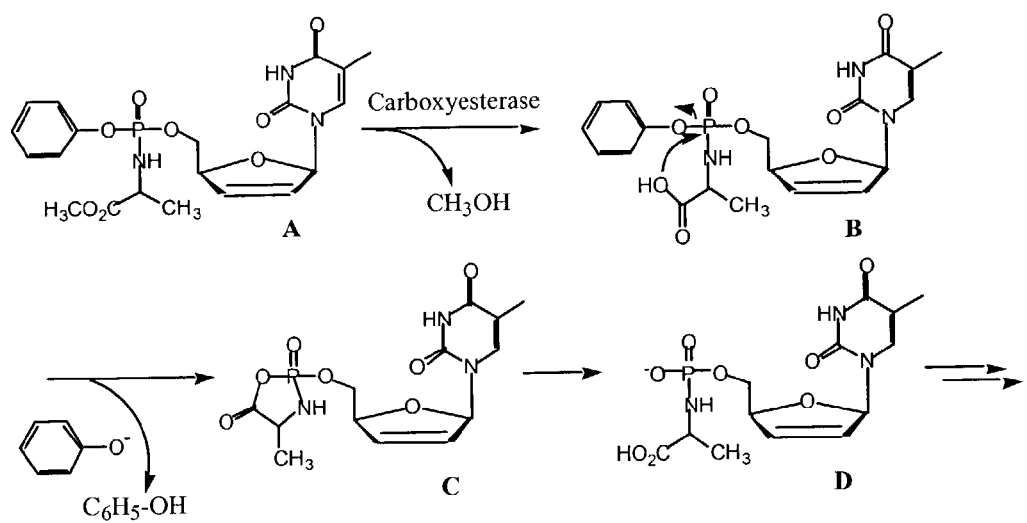
FIG. 1 is a schematic diagram of a prior art-proposed metabolic pathway for aryl phosphate derivatives of d4T.

All scientific and technical terms used in this application have meanings commonly used in the art unless otherwise specified. As used in this application, the following words or phrases have the meanings specified.

As used herein, the term "about" applies to all numeric values, whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

As used herein, "pharmaceutically acceptable salt thereof" includes an acid addition salt or a base salt.

As used herein, "pharmaceutically acceptable carrier" includes any material which, when combined with a compound of the invention, allows the compound to retain biological activity, such as the ability to induce apoptosis of leukemia or breast tumor cells, and is non-reactive with the subject's immune system. Examples include, but are not limited to, any of the standard pharmaceutical carriers such as a phosphate buffered saline solution, water, emulsions such as oil/water emulsions, and various types of wetting agents. Compositions comprising such carriers are formulated by well known conventional methods (see, for example, Remington's Pharmaceutical Sciences, Chapter 43, 14th Ed., Mack Publishing Co., Easton, Pa.).

The term "amino acid" refers to any of the naturally occurring amino acids, as well as their opposite enantiomers or racemic mixture of both enantiomers, synthetic analogs, and derivatives thereof. The term includes, for example, α-, β-, γ-, δ-, and ω-amino acids. Suitable naturally occurring amino acids include glycine, alanine, valine, leucine, isoleucine, proline, threonine, serine, methionine, cysteine, aspartic acid, asparagine, glutamic acid, glutamine, arginine, lysine, phenylalanine, tryptophan, tyrosine, and histidine. Synthetic, or unnatural, amino acids such as, for example, trifluoroleucine, p-fluorophenylalanine, and 3-triethylalanine can be used. The term amino acid includes esters of the amino acids. Esters include lower alkyl esters in which the alkyl group has one to seven carbon atoms, preferably one to four carbon atom such as, for example, methyl, ethyl, propyl, and butyl. The amino group of the amino acid or ester thereof is attached to the phosphate group in Formula I.

The term "electron-withdrawing groups" includes groups such as halo (—Br, —Cl, —I, —F) —NO$_2$, —CN, —SO$_3$H, —COOH, —CHO, —COR (where R is a (C$_1$ to C$_4$) alkyl), and the like.

The term "halo" or "halogen" is used to describe an atom selected from the group of Bromine (Br), Chlorine (Cl), Fluorine (F) and Iodine (I).

Compounds of the Invention

Compounds of the invention include compounds of Formula I below

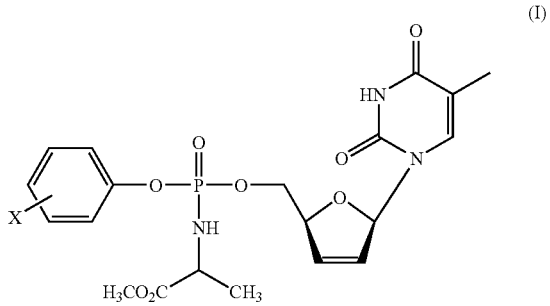

wherein X is an electron withdrawing group and R$_2$ is an amino acid residue. Compounds of the invention can also have more than one electron withdrawing group, X, substituted on the phenyl ring. One embodiment of the invention includes compounds of Formula I where X is a halo, but not F. In another embodiment of the invention, X is selected from Br, Cl, I, and NO$_2$, preferably from Br and Cl. In a further embodiment of the invention, the compound contains two electron withdrawing groups, X, for example, at the 2 and 5 position, preferably a Cl at both the 2 and 5 position. In yet another embodiment of the invention, the compound of the invention includes a Cl at the 4 position, or a Br at the 4 position. One embodiment of the invention includes compounds of Formula I where R$_2$ is —NHCH(CH$_3$)COOCH$_3$.

One embodiment of the invention, the d4T derivatives have aryl-phosphate substitution, with the aryl group having an electron-withdrawing substitution, such as an ortho or para-substitution with a halogen (Br, Cl, F, I) or with NO$_2$ substitution. One example, a compound of Formula III, is shown below, where R$_2$ is an amino acid residue that may be esterified or substituted, for example —NHCH(CH$_3$)COOCH$_3$ or pharmaceutically acceptable salts or esters thereof.

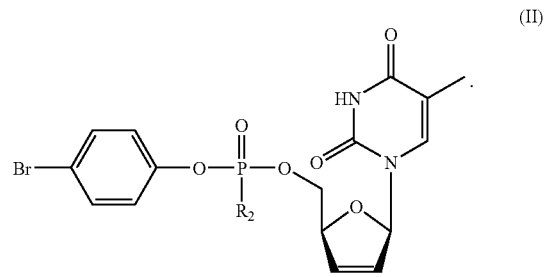

A compound of the formula II, is referred to herein as "compound 113".

The compounds of the invention, as discussed more fully in the Examples below, include derivatives of 2'3'-didehydro-2'3'-dideoxythymidine (hereinafter "d4T") having potent antiviral activities. Preferred is halogen substitution, and most preferred is para-bromo substitution.

It is thought that the compound of Formula III with a single para-bromine group in the phenyl moiety contributes to its ability to undergo rapid hydrolysis yielding the key active metabolite alaninyl-stavudine-monophosphate (ala-STV-MP) (Venkatachalam et al., 1998, *Biorg. Med. Chem. Lett.*, 8:3121–25).

Synthesis of the d4T derivatives:

The d4T derivatives can be prepared as known to those of skill in the art, for example, as follows. d4T can be prepared from thymidine by the procedures discussed in Mansuri, et al., 1989, *J. Med. Chem.* 32:461, the disclosure of which is incorporated herein by reference. Appropriately substituted aryl phosphorochloridate can be prepared by the procedures discussed in McGuigan, et al., 1992, *Antiviral Res.*, 17:311, the disclosure of which is incorporated herein by reference. The phosphorochloridate is added to a solution of d4T in anhydrous THF containing N-methylimidazole to form the desired product.

The d4T derivatives are administered to patients in the form of suitable compositions containing the d4T or AZT derivative as an active agent along with a pharmaceutically acceptable carrier, adjuvant, or diluent. Sustained release dosage forms may be used if desired. The compositions are administered to a patient in need of the anti-viral activity in a suitable anti-viral amount, for example, sufficient to inhibit the HIV reverse transcriptase and/or inhibit replication of HIV in a host cells. The dose is administered according to a suitable dosage regimen.

Salts

The compounds of the invention are capable of forming both pharmaceutically acceptable acid addition and/or base salts. Base salts are formed with metals or amines, such as alkali and alkaline earth metals or organic amines. Examples of metals used as cations are sodium, potassium, magnesium, calcium, and the like. Also included are heavy metal salts such as, for example, silver, zinc, cobalt, and cerium. Examples of suitable amines are N,N'-dibenzylethylenediamine, chloroprocaine, choline, diethanolamine, ethylenediamene, N-methylglucamine, and procaine.

Pharmaceutically acceptable acid addition salts are formed with organic and inorganic acids. Examples of suitable acids for salt formation are hydrochloric, sulfuric, phosphoric, acetic, citric, oxalic, malonic, salicylic, malic, gluconic, fumaric, succinic, ascorbic, maleic, methanesulfonic, and the like. The salts are prepared by contacting the free base form with a sufficient amount of the desired acid to produce either a mono or di, etc. salt in the conventional manner. The free base forms can be regenerated by treating the salt form with a base. For example, dilute solutions of aqueous base can be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for the purposes of the invention.

Methods of the Invention

In accordance with one aspect of the invention, compounds of the invention are used in methods of inhibiting virus replication in a cell infected with a resistant strain of HIV. Inhibiting virus replication includes, but is not limited to, diminishing the rate at which the virus replicates, diminishing the rate at which new cells are infected.

In accordance with another aspect of the invention, compounds of the invention are used in methods of treating a patient infected with a resistant strain of HIV. Treating a patient infected with a resistant strain of HIV includes, but is not limited to, slowing the progression of the infection by the resistant strain of HIV, and decreasing the symptoms associated with the infection by the resistant strain of HIV.

As used herein, "a resistant strain of HIV" is a strain of HIV that can be identified by its genetic makeup as a strain that is known to be resistant to one or more anti-HIV drugs, by clinically isolating a strain of HIV from an infected individual who is not responding or has not responded to at least one treatment course ("non-responder"). Resistant strains of HIV can be resistant to one or more classes of anti-HIV drugs including for example protease inhibitors, nucleoside reverse transcriptase inhibitors (NRTIs), and non-nucleoside reverse transcriptase inhibitors (NNRTIs). Examples of resistant strains of HIV include but are not limited to A17 (NNRTI resistant), A17-variant (NNRTI-resistant), and RT-MDR (NRTI-resistant and NNRTI-resistant). Examples of resistant strains of HIV, classification thereof, and methods of testing for resistant strains can be found in Shafer et al, (2001) A guide to HIV-1 reverse transcriptase and protease sequencing for drug resistance studies. *Human Retroviruses and AIDS*, Theoretical Biology and Biophysics. Los Alamos National Laboratories and Parikh et al. 2001 Mutations in Retroviral Genes Associated with Drug Resistance. *Human Retroviruses and AIDS*, Theoretical Biology and Biophysics. Los Alamos National Laboratories.

Administration Methods

The compounds of the present invention can be formulated as pharmaceutical compositions and administered to a mammalian host, including a human patient, in a variety of forms adapted to the chosen route of administration. The compounds are preferably administered in combination with a pharmaceutically acceptable carrier, and can be combined with or conjugated to specific delivery agents, including targeting antibodies and/or cytokines.

The compounds can be administered by known techniques, such as orally, parentally (including subcutaneous injection, intravenous, intramuscular, intrasternal or infusion techniques), by inhalation spray, topically, by absorption through a mucous membrane, or rectally, in dosage unit formulations containing conventional non-toxic pharmaceutically acceptable carriers, adjuvants or vehicles. Pharmaceutical compositions of the invention can be in the form of suspensions or tablets suitable for oral administration, nasal sprays, creams, sterile injectable preparations, such as sterile injectable aqueous or oleagenous suspensions or suppositories.

For oral administration as a suspension, the compositions can be prepared according to techniques well-known in the art of pharmaceutical formulation. The compositions can contain microcrystalline cellulose for imparting bulk, alginic acid or sodium alginate as a suspending agent, methylcellulose as a viscosity enhancer, and sweeteners or flavoring agents. As immediate release tablets, the compositions can contain microcrystalline cellulose, starch, magnesium stearate and lactose or other excipients, binders, extenders, disintegrants, diluents, and lubricants known in the art.

For administration by inhalation or aerosol, the compositions can be prepared according to techniques well-known in the art of pharmaceutical formulation. The compositions can be prepared as solutions in saline, using benzyl alcohol or other suitable preservatives, absorption promoters to enhance bioavailability, fluorocarbons, or other solubilizing or dispersing agents known in the art.

For administration as injectable solutions or suspensions, the compositions can be formulated according to techniques well-known in the art, using suitable dispersing or wetting and suspending agents, such as sterile oils, including synthetic mono- or diglycerides, and fatty acids, including oleic acid.

For rectal administration as suppositories, the compositions can be prepared by mixing with a suitable non-irritating excipient, such as cocoa butter, synthetic glyceride esters or polyethylene glycols, which are solid at ambient temperatures, but liquefy or dissolve in the rectal cavity to release the drug.

Preferred administration routes include orally, parenterally, as well as intravenous, intramuscular or subcutaneous routes.

More preferably, the compounds of the present invention are administered parenterally, i.e., intravenously or intraperitoneally, by infusion or injection. In one embodiment of the invention, the compounds can be administered directly to a tumor by tumor injection. In another embodiment of the invention, the compounds can be administered using systemic delivery by intravenous injection.

Solutions or suspensions of the compounds can be prepared in water, isotonic saline (PBS), and optionally mixed with a nontoxic surfactant. Dispersions can also be prepared in glycerol, liquid polyethylene, glycols, DNA, vegetable oils, triacetin and mixtures thereof. Under ordinary conditions of storage and use, these preparations can contain a preservative to prevent the growth of microorganisms.

The pharmaceutical dosage form suitable for injection or infusion use can include sterile, aqueous solutions, dispersions, or sterile powders comprising an active ingredient which are adapted for the extemporaneous preparation of sterile injectable or infusible solutions or dispersions. The final dosage form should be sterile, fluid and stable under the conditions of manufacture and storage. The liquid carrier or vehicle can be a solvent or liquid dispersion medium comprising, for example, water, ethanol, a polyol such as glycerol, propylene glycol, or liquid polyethylene glycols, and the like, vegetable oils, nontoxic glyceryl esters, and suitable mixtures thereof. The proper fluidity can be maintained, for example, by the formation of liposomes, by the maintenance of the required particle size, in the case of dispersion, or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers, or sodium chloride. Prolonged absorption of the injectable compositions can be brought about by the inclusion in the composition of agents delaying absorption such as, for example, aluminum monosterate hydrogels and gelatin.

Sterile injectable solutions are prepared by incorporating the conjugates in the required amount in the appropriate solvent with various other ingredients as enumerated above and, as required, followed by filter sterilization. In the case of sterile powders for the preparation of sterile injectable solutions, the preferred methods of preparation are vacuum drying and freeze-drying techniques, which yield a powder of the active ingredient plus any additional desired ingredient present in the previously sterile-filtered solutions.

Pharmacokinetics

Previous in vitro studies have shown that an electron withdrawing group at the para position of the phenyl group enhances the rate of hydrolysis and thereby enhances production of a key metabolite alaninyl-d4T-monophosphate (Ala-d4T-MP) relative to the unsubstituted aryl phosphate derivative (Venkatachalam et al., 1998, *Bioorg. Med. Chem. Lett.,* 8:312; Vig et al., 1998, *Antiviral Chem. Chemother.,* 9:445; and U.S. Pat. No. 6,030,957 (Uckun et al.)).

The anti-viral agent d4T-5'-[p-bromophenyl methoxyalaninyl phosphate] is quickly metabolized in vivo to form two metabolites: 2',3'-didehydro-3'-deoxythymidine (d4T) and alaninyl-d4T-monophosphate (Ala-d4T-MP) as shown in FIG. 1. Ala-d4T-MP can also be metabolized further to yield d4T. The metabolite d4T had not been found in earlier in vitro studies with cells.

d4T-5'-[p-bromophenyl methoxyalaninyl phosphate] readily metabolizes in either plasma or whole blood to form Ala-d4T-MP and a small amount of d4T. Ala-d4T-MP is stable both in plasma and in whole blood. These results indicate that other enzymes (e.g., liver enzymes) are needed to form d4T by hydrolysis of either Ala-d4T-MP or d4T-5'-[p-bromophenyl methoxyalaninyl phosphate]. This hypothesis is consistent with the formation of a significant amount of d4T after incubation of d4T-5'-[p-bromophenyl methoxyalaninyl phosphate] with a liver homogenate.

Elimination Half-Life

The elimination half-life of intravenously administered d4T is fairly similar to the elimination half-life of d4T formed after intravenous administration of Ala-d4T-MP ($t_{1/2}$ of 30.3 minutes vs. 34.0 minutes) as shown in the Examples below. In contrast, the elimination half-life for d4T formed after intravenous administration of d4T-5'-[p-bromophenyl methoxyalaninyl phosphate] was significantly prolonged ($t_{1/2}$ of 114.8 minutes). Similarly, the elimination half-life for Ala-d4T-MP formed from d4T-5'-[p-bromophenyl methoxyalaninyl phosphate] was significantly longer than the $t_{1/2}$ for Ala-d4T-MP administered intravenously ($t_{1/2}$ of 129.2 minutes vs. 28.5 minutes). The intravenous administration of d4T-5'-[p-bromophenyl methoxyalaninyl phosphate] results in prolonged systemic exposure to both Ala-d4T-MP and d4T compared to administration of equimolar dose of Ala-d4T-MP or d4T due to apparently longer elimination half-lives of d4T-5'-[p-bromophenyl methoxyalaninyl phosphate]-derived metabolites.

Following intravenous administration, the elimination half-life ($t_{1/2}$) of d4T-5'-[p-bromophenyl methoxyalaninyl phosphate] was 3.5 minutes with a systemic clearance (CL) of 160.9 ml/min/kg. Different estimates for systemic clearance (CL) values were obtained for the two diastereomers of d4T-5'-[p-bromophenyl methoxyalaninyl phosphate] (d4T-5'-[p-bromophenyl methoxyalaninyl phosphate]A is 208.2 ml/min/kg and d4T-5'-[p-bromophenyl methoxyalaninyl phosphate]B is 123.9 ml/min/kg), but both were completely metabolized within 30 minutes. d4T-5'-[p-bromophenyl methoxyalaninyl phosphate] was converted to the active metabolites Ala-d4T-MP (23%) and d4T (24%). The $t_{max}$ values for Ala-d4T-MP and d4T formed from intravenously administered d4T-5'-[p-bromophenyl methoxyalaninyl phosphate] were 5.9 minutes and 18.7 minutes, respectively.

Bioavailability

Orally administered d4T-5'-[p-bromophenyl methoxyalaninyl phosphate] also yielded Ala-d4T-MP and d4T as the major metabolites. No parent d4T-5'-[p-bromophenyl methoxyalaninyl phosphate] was detectable in the blood after oral administration. Although d4T-5'-[p-bromophenyl methoxyalaninyl phosphate] is stable in gastric fluid and can be absorbed in the stomach, it can quickly hydrolyze in blood. On the other hand, d4T-5'-[p-bromophenyl methoxyalaninyl phosphate] decomposes readily in intestinal fluid to form Ala-d4T-MP. This metabolite can be absorbed in the intestine and then further metabolized to yield d4T in the blood. The $t_{max}$ and $t_{1/2}$ values for d4T in mice were longer when derived from orally administered d4T-5'-[p-bromophenyl methoxyalaninyl phosphate] (42.4 minutes and 99.0 minutes, respectively) than from orally administered d4T (5 minutes and 18 minutes, respectively). The $t_{max}$ value is higher but the $t_{1/2}$ value is lower for orally administered d4T-5'-[p-bromophenyl methoxyalaninyl phosphate] compared to intravenously administered d4T-5'-[p-bromophenyl methoxyalaninyl phosphate]. The estimated bioavailabilities of Ala-d4T-MP and d4T were approximately 12% and 48%, respectively, after oral administration of d4T-5'-[p-bromophenyl methoxyalaninyl phosphate]. However, the bioavailability of d4T metabolized from d4T-5'-[p-bromophenyl methoxyalaninyl phosphate] (48%) was lower than that of orally administered d4T (98%).

The in vivo pharmacokinetics, metabolism, toxicity, and antiretroviral activity of d4T-5'[p-bromophenyl methoxyalaninyl phosphate] in rodent species has been investigated (Uckun et al., *Arzneimittelforschung/Drug Research,* 2002, (in press)). In mice and rats, d4T-5'-[p-bromophenyl methoxyalaninyl phosphate] was very well tolerated without any detectable acute or subacute toxicity at single intraperitoneal or oral bolus dose levels as high as 500 mg/kg (Uckun et al., 2002, (Supra)). Notably, daily administration of d4T-5'-[p-bromophenyl methoxyalaninyl phosphate] intraperitoneally or orally for up to 8 consecutive weeks was not associated with any detectable toxicity in mice or rats at cumulative dose levels as high as 6.4 g/kg (Uckun et al., 2002, (Supra)). In accordance with its safety profile in rodent species, a four-week d4T-5'-[p-bromophenyl methoxyalaninyl phosphate] treatment course with twice daily administration of hard gelatin capsules containing 25 mg/kg–100 mg/kg d4T-5'-[p-bromophenyl methoxyalaninyl phosphate] was very well tolerated by dogs and cats at cumulative dose levels as high as 8.4 g/kg (Uckun et al., *Antimicrob. Agents Chemother.* (submitted 2002)).

Useful Dose

When used in vivo to inhibit resistant HIV strains and/or non-B subtype HIV, the administered dose is that effective to have the desired effect, such as sufficient to reduce or eliminate one or more symptom of hemorragic fever. Appropriate amounts can be determined by those skilled in the art, extrapolating using known methods and relationships, from the in vivo animal model data provided in the Specification and Examples.

In general, the dose of the aryl phosphate derivatives of d4T effective to achieve therapeutic treatment, including reduction or prevention of symptoms or effects of HIV infection, such as increased survival time, is in the approximate range of about 1–500 mg/kg body weight/dose, preferably about 10–100 mg/kg body weight/dose, and approximately 800–1000 mg/kg body weight per week of a cumulative dose.

The effective dose to be administered will vary with conditions specific to each patient. In general, factors such as the viral burden, host age, metabolism, sickness, prior exposure to drugs, and the like, contribute to the expected effectiveness of a drug. One skilled in the art will use standard procedures and patient analysis to calculate the appropriate dose, extrapolating from the data provided in the Examples. In general, a dose which delivers about 1–100 mg/kg body weight is expected to be effective, although more or less may be useful.

In addition, the compositions of the invention may be administered in combination with other therapies. In such combination therapy, the administered dose of the compounds may be less than for single drug therapy.

EXAMPLES

The invention can be further clarified by reference to the following Examples, which serve to exemplify some of the embodiments, and not to limit the invention in any way.

Example 1

Synthesis and Characterization of d4T Derivatives d4T 1 was prepared from thymidine following the procedure of Mansuri et.al., 1989, *J. Med. Chem.*, 32:461. Appropriately substituted phenyl methoxyalaninyl phosphorochloridates were also prepared according to the method reported by McGuigan et al., 1992, *Antiviral Res.*, 17:311. Compounds 2–4 were synthesized as outlined below in Scheme 1.

Scheme 1

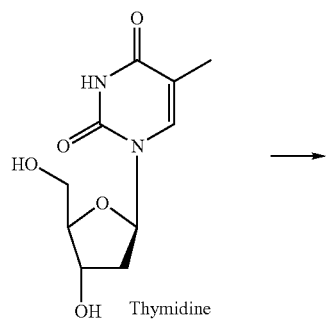
Thymidine

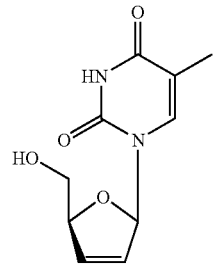
d4T (1)

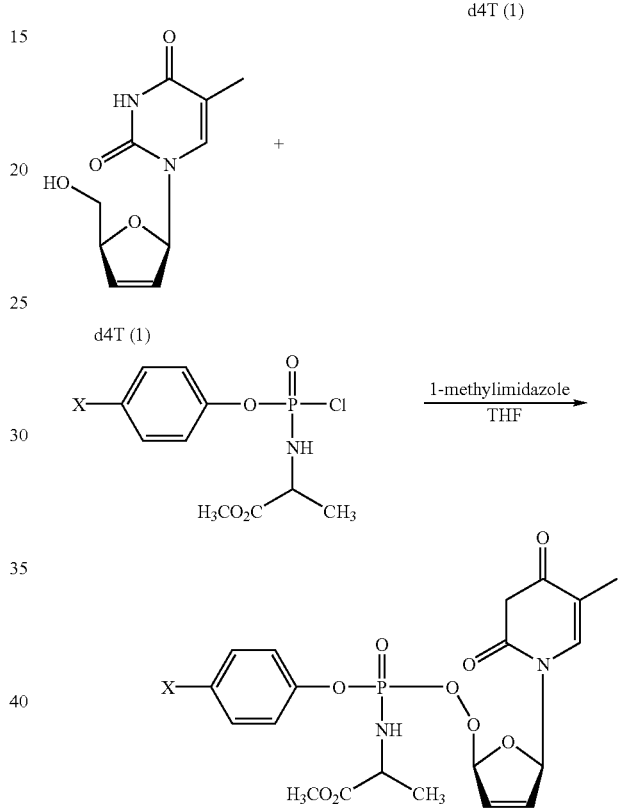

2: X = H
3: X = OCH₃
4: X = Br

Phenylmethoxyalaninyl phosphorochloridate was added to the solution of d4T and 1-methylimidazole in anhydrous THF and the mixture was stirred at room temperature for 5–6 hours. Work up of the reaction mixture furnished the required derivatives in good yields. Column chromatography was applied to obtain pure compounds.

Physical data of the synthesized compounds was determined by HPLC conducted by using C18 4×250 mm LiChrospher column eluted with 70:30 water/acetonitrile at the flow rate of 1 ml/minute. The purity of the following compounds exceeded 96% by HPLC. $^{13}$C NMR peaks labeled by stars are split due to diastereomers. Physical data for the compounds is given below.

Compound 2: yield: 81%; IR (Neat): 3222, 2985, 2954, 1743, 1693, 1593, 1491, 1456, 1213, 1153, 1039, 931, 769 cm$^{-1}$; $^{1}$H NMR (CDCl$_3$) δ 9.30 (br s, 1H), 7.30–7.10 (m, 6H), 6.85–6.82 (m, 1H), 6.36–6.26 (m, 1H), 5.91–5.85 (m, 1H), 5.00 (br m, 1H), 4.19–3.68 (m, 4H), 3.72, 3.71 (s, 3H), 1.83, 1.80 (d, 3H), 1.38–1.25 (m, 3H); $^{13}$C NMR(CDCl$_3$) δ 173.9, 163.7, 150.7, 149.7, 135.7*, 133.2*, 129.6*, 127.3*, 125.0*, 120.0, 111.1, 89.6*, 84.5*, 66.9*, 52.5*, 50.0*, 20.9 and 12.3; $^{31}$P NMR(CDCl$_3$) δ 2.66, 3.20; MALDI-TOF mass m/e 487.9 (M+Na); HPLC retention time: 5.54 & 5.85 minutes.

Compound 3: yield: 92%; IR (Neat): 3223, 3072, 2999, 2953, 2837, 1743, 1693, 1506, 1443, 1207, 1153, 1111, 1034, 937, 837 and 756 cm$^{-1}$; $^{1}$H NMR(CDCl$_3$) δ 9.40 (br s, 1H), 7.30–7.00 (m, 5H), 6.83–6.81 (m, 1H), 6.37–6.27 (m, 1H ), 5.91–5.86 (m, 1H), 5.00 (br m, 1H), 4.40–4.30 (m, 2H), 4.20–4.10 (m, 2H), 3.95–3.93 (s, 3H), 3.82–3.80 (s, 3H), 1.85–1.81 (s, 3H) and 1.39–1.29 (m, 3H); $^{13}$C NMR (CDCl$_3$) δ 174.0, 163.9, 156.6, 150.8, 143.5, 135.8*, 133.3*, 127.4*, 121.2*, 114.5, 111.2, 89.7*, 84.5, 66.9*, 55.5, 52.5, 50.6*, 20.9, and 12.3; $^{31}$P NMR(CDCl$_3$) δ 3.82, 3.20; MALDI-TOF mass m/e 518.2 (M+Na); HPLC retention time: 5.83 & 6.26 minutes.

Compound 4: yield: 83%; IR (Neat): 3203, 3070, 2954, 2887, 2248, 1743, 1693, 1485, 1221, 1153, 1038, 912, 835, 733 cm$^{-1}$; $^{1}$H NMR(CDCl$_3$) δ 9.60–9.58 (br s, 1H), 7.45–7.42 (m, 2H), 7.30–7.09 (m, 4H), 6.37–6.27 (m, 1H), 5.93–5.88 (m, 1H), 5.04–5.01 (br m, 1H), 4.35–4.33 (m, 2H), 4.27–3.98 (m, 2H), 3.71–3.70 (s, 3H), 1.85–1.81 (s, 3H), 1.37–1.31 (m, 3H); $^{13}$C NMR(CDCl$_3$) δ 173.7, 163.8, 150.8, 149.7*, 135.6*, 133.1*, 127.4*, 121.9*, 118.0, 111.2*, 89.7*, 84.4*, 67.8*, 52.5, 50.0*, 20.7, and 12.3; $^{31}$P NMR(CDCl$_3$) δ 3.41, 2.78; MALDI-TOF mass m/e 567.1 (M+Na); HPLC retention time: 12.04 & 12.72 minutes.

Example 2

Susceptibility of Compounds 2–4 to Hydrolysis.

FIGS. 2A and 2B show a schematic representation of the electronic effects of the para substituent in the phenyl ring of metabolite precursor B (see FIG. 1). To assess the susceptibility of compounds to hydrolysis, Compounds 2–4 were dissolved in methanol and then treated with 0.002 N NaOH. The concentrations were kept constant and the generation of the hydrolysis product A-d4T-MP was monitored using HPLC. A Lichrospher column (C18) was used for the HPLC runs. The column was eluted under isocratic conditions using the solvent mixture 70:30 water/acetonitrile, and the elution profile is shown in FIG. 2C.

Hydrolysis of compounds was tested in a porcine liver esterase system. The data are shown in FIG. 2C. Compounds 2 and 4 (1 mM in Tris-HCl) were incubated with 100 U of porcine liver esterase (Sigma) in Tris-HCl buffer (pH 7.4) for 2 hours at 37° C. Reaction was stopped by adding acetone and chilling the reaction mixture. Following centrifugation at 15,000×g, 0.1 mL aliquots of the reaction mixture were examined for the presence of the active metabolite A-d4T-MP by using a quantitative analytical HPLC method capable of detecting 50 pmols of the metabolite. The 0.1 mL aliquot of the reaction product of compound 4 contained 1.4 nmols of A-d4T-MP, wheras no metabolite was detected in the reaction product of compound 2.

As shown in FIGS. 2A and 2B, the presence of an electron withdrawing substituent at the para position of the phenyl moiety is likely to increase the hydrolysis rates of the phenoxy group in the metabolite precursor B (FIGS. 2A and 2B) generated by the carboxyesterase-dependent first step (FIG. 1, A to B) of the metabolic pathway of phenyl phosphate derivatives of d4T. A single bromo substitution at the para position of the phenyl ring would not interfere with the recognition and hydrolysis of this compound by the carboxyesterase (Step A to B in FIG. 1). An electronic effect induced by the electron-withdrawing para-bromo substituent would result in enhanced hydrolysis of phenoxy group C yielding D and subsequently E, the precursors of the key metabolite A-d4T-MP. In order to test this hypothesis, we compared the unsubstituted compound 2, para-methoxy (OCH$_3$) substituted compound 3, and para-bromo substituted compound 4 (=d4T-5'-[p-bromo-phenylmethoxyalaninyl phosphate] or d4T-pBPMAP), for their rate of chemical hydrolysis after treatment with 0.002 N NaOH by measuring the generation of alaninyl-d4T-monophosphate (A-d4T-MP).

As shown in FIG. 2C, compound 4 with a para-bromo substitent showed a much faster hydrolysis rate than the unsubstituted compound 2, whereas compound 3 with the electron donating substituent —OCH$_3$ at para position had a slower hydrolysis rate than either of those two compounds. Similarly, the lead compound 4 was more sensitive to enzymatic hydrolysis by porcine liver esterase than compound 2 (FIG. 2D).

Example 3

Intracellular metabolism of compounds 2–4 in TK-deficient CEM cells

Figure 3:
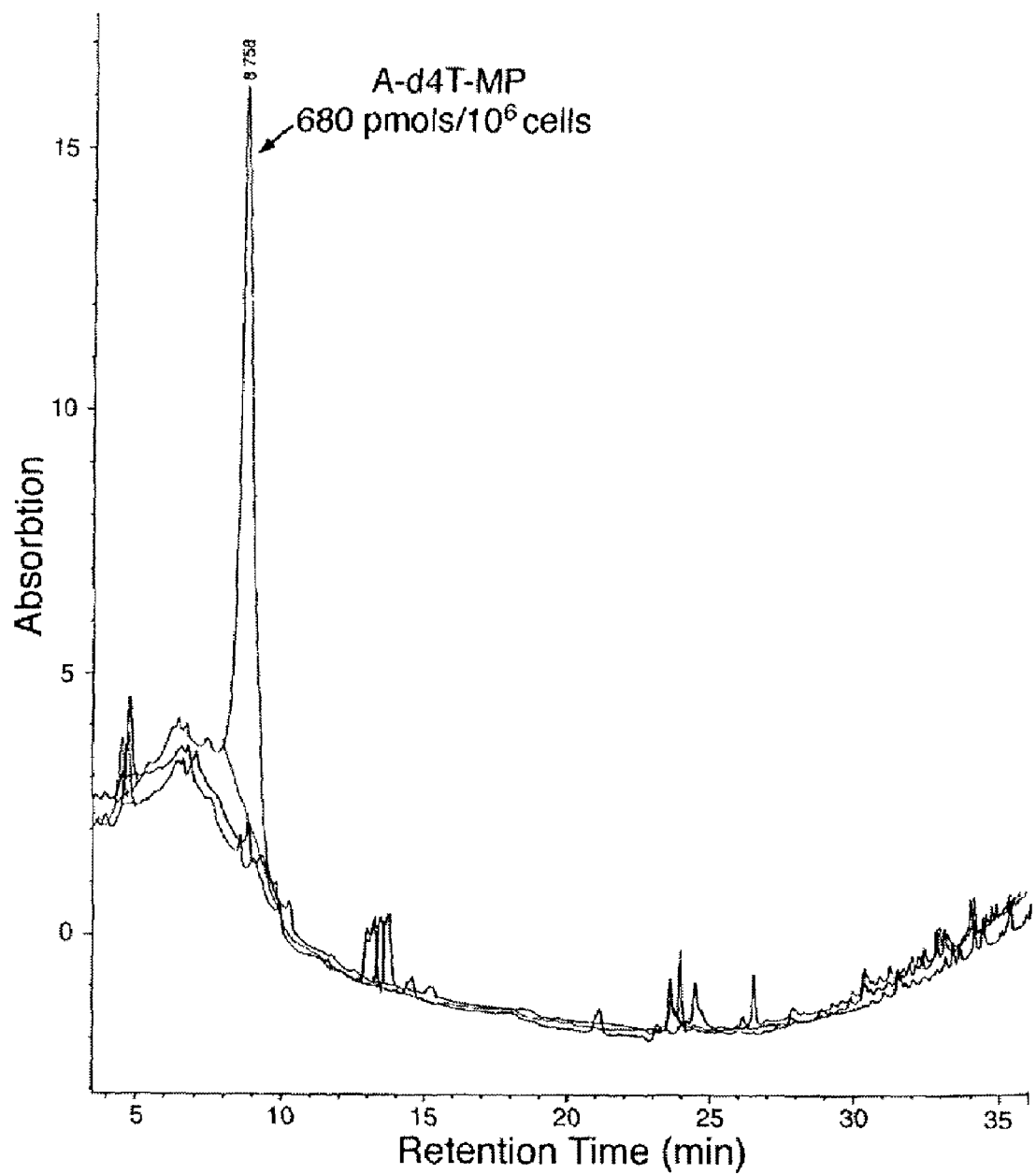
FIG. 3 is an elution profile showing the intracellular hydrolysis of compounds 2–4 in TK-deficient CEM cells. A metabolite peak with corresponding to 680 pmols of A-d4T-MP was detected only in aliquots from CEM cell lysates incubated with compound 4.
Figure 4A:
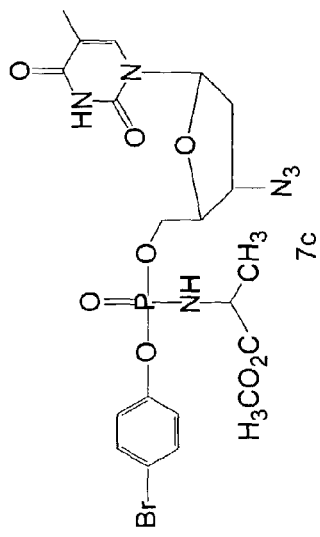
FIGS. 4A–4F show the chemical structures of compound 6c (FIG. 4A) and compound 7c (FIG. 4B); the anti-HIV activity against HTLV$_{IIIB}$ in PBMNC and TK-deficient CEM T-cells for compound 6c (FIG. 4C) and for compound 7c (FIG. 4D); and the antiviral activity against HIV-1 (HTLV$_{IIIB}$), HIV-2 and RTMDR-1 for compound 6c (FIG. 4E) and compound 7c (FIG. 4F). Antiviral activity was expressed as % inhibition of HIV replication as measured by RT activity in infected cells.
Figure 4C:
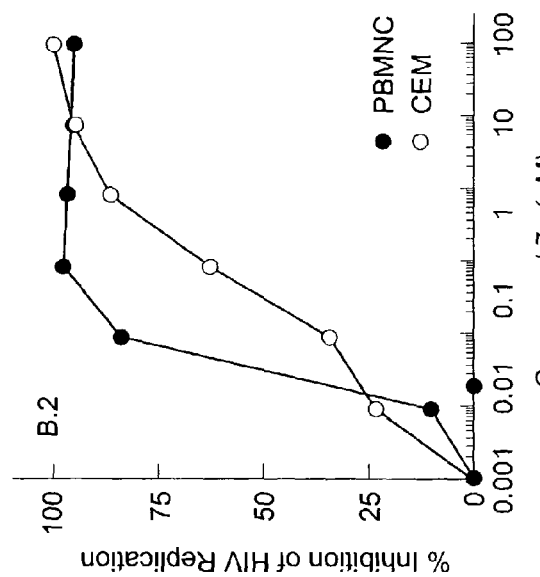
Figure 4B:
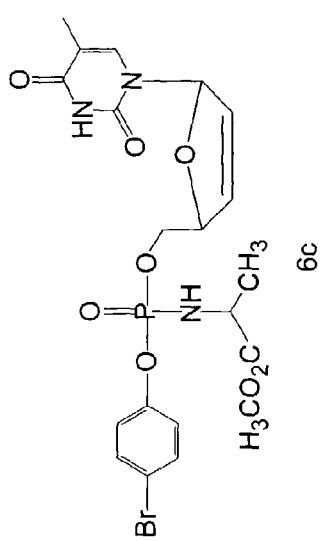
Figure 4D:
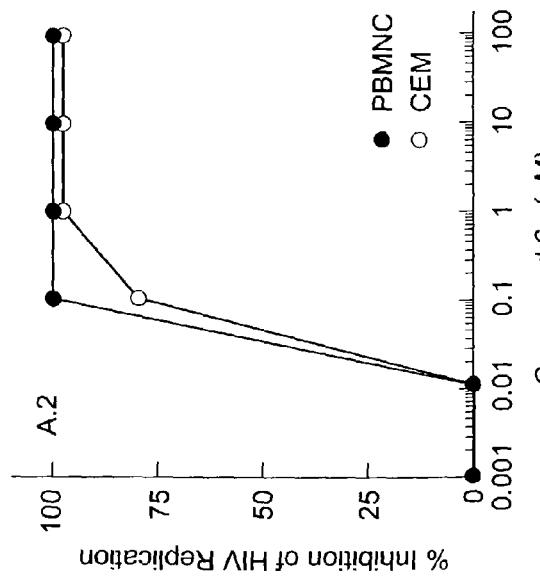
Figure 4F:
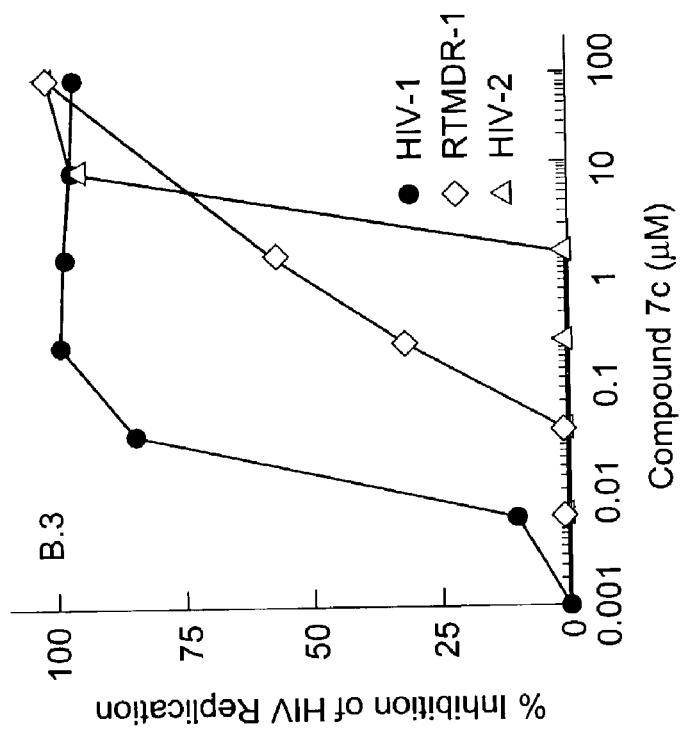
Figure 4E:
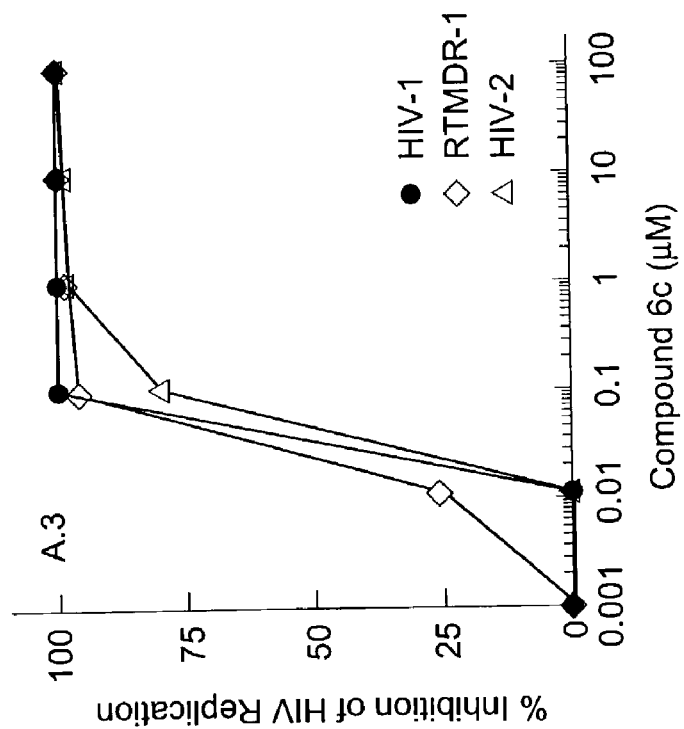

To analyze the intracellular metabolism of compounds 2–4 in TK-deficient cells, 1×10$^6$ CEM cells were incubated with compounds 2–4 (100 μM) for 3 hours and subsequently examined the formation of the partially hydrolyzed phosphate diester metabolite, alaninyl d4T monophosphate by HPLC. Notably, the amount of this metabolite in CEM cells treated with compound 4 was substantially greater than in CEM cells treated with compound 2 or 3 (680 pmol/10$^6$ cells vs <50 pmol/10$^6$ cells; FIG. 3).

CEM cells were cultured in a medium composed of RPMI, 10% fetal bovine serum, and 1% penicillin/streptomycin. Ten million cells at a density of 10$^6$ cells/mL were incubated with 100 μM of these compounds for 3 hours at 37° C. After incubation, cells were washed twice with ice-cold PBS, and extracted by addition of 0.5 mL of 60% methanol. Cell lysates were kept at −20° C. overnight, after which lysates were centrifuged at 15000×g for 10 minutes to remove the cell debris. One hundred μL aliquots of these lysates were injected directly to HPLC. The HPLC system consisted of a Hewlett Packard (HP) 1100 series equipped with a quarternary pump, an auto sampler, an electronic degasser, a diode array detector, and a computer with a chemstation software program for data analysis. The samples were eluted on a 250×4.6 mm Sulpelco LC-DB C18 column. A solvent gradient was utilized to resolve the metabolite from the parent compound, which consisted of a mixture of methanol and 10 mM ammonium phosphate (pH 3.7). The gradient ran at a flow rate of 1 mL/minute from 5 to 35% methanol for the first 10 minutes, kept at 35% methanol for 5 minutes, and finished with a linear gradient from 35 to 100% methanol in the next 20 minutes. The detection wavelength was set at 270 nm. A metabolite peak with a retention time of 8.7 minutes corresponding to 680 pmols of A-d4T-MP was detected only in aliquots from CEM cell lysates incubated with compound 4.

Example 4

Anti-HIV Activity of Compounds 2–4

Because of its enhanced susceptibility to hydrolysis, compound 4 was postulated to be a more potent anti-HIV agent than the other compounds. Compounds 2–4 as well as the parent compound d4T (1) were tested for their ability to inhibit HIV replication in peripheral blood mononuclear cells and TK-deficient CEM T-cells using previously described procedures (Zarling et.al., 1990, *Nature*, 347:92; Erice et.al., 1993, *Antimicrob.Agents Chemother.*, 37:835–838; Uckun et.al., 1998, *Antimicrob. Agents Chemother.*, 42:383). Percent inhibition of viral replication was calculated by comparing the p24 and RT activity values from the test substance-treated infected cells with those from untreated infected cells. In parallel, the cytotoxicity of the compounds was examined using a microculture tetrazolium assay (MTA) of cell proliferation, as described in the Zarling, Enrice, and Uckun articles Supra).

The similarity of the $IC_{50}$ values for inhibition of HIV-1 replication shown in Table 1, provide evidence that the d4T-aryl phosphate derivatives were not more potent than the parent compound d4T when tested in HIV-1-infected peripheral blood mononuclear cells. In accord with previous reports, the ability of d4T to inhibit HIV-1 replication was substantially reduced in TK-deficient CEM cells. Whereas the $IC_{50}$ value for inhibition of p24 production by d4T was 18 nM in peripheral blood mononuclear cells, it was 556 nM in TK-deficient CEM cells. Similarly, the $IC_{50}$ value for inhibition of RT activity increased from 40 nM to 2355 nM (Table 1). While all 3 aryl phosphate derivatives were more potent than d4T in TK-deficient CEM cells, compound 4 (d4T-5'-[p-bromo phenylmethoxyalaninyl phosphate]) having a para-bromo substituent in the aryl moiety, was 12.6-fold more potent in inhibiting p24 production ($IC_{50}$ values: 44 nM vs 556 nM) and 41.3-fold more potent in inhibiting the RT activity ($IC_{50}$ values: 57 nM vs 2355 nM) than d4T (Table 1).

TABLE 1

| | | PBMNC | | | CEM | | |
|---|---|---|---|---|---|---|---|
| Compound | X | $IC_{50}$ [p24] | $IC_{50}$ [RT] | $IC_{50}$ [MTA] | $IC_{50}$ [p24] | $IC_{50}$ [RT] | $IC_{50}$ [MTA] |
| 1 (= d4T) | | 0.018 | 0.040 | >10 | 0.556 | 2.355 | >10 |
| 2 | H | ND | ND | >10 | 0.145 | 0.133 | >10 |
| 3 | —OCH$_3$ | 0.033 | 0.033 | >10 | 0.106 | 0.320 | >10 |
| 4 | Br | 0.022 | 0.042 | >10 | 0.044 | 0.057 | >10 |

None of the tested compounds exhibited any detectable cytotoxicity to peripheral blood mononuclear cells or CEM cells at concentrations as high as 10,000 nM, as determined by MTA. Intriguingly, compound 3 with a para-methoxy substituent in the aryl moiety was 5.6-fold less effective than compound 4 in inhibiting the RT activity in HIV-infected TK-deficient CEM cells ($IC_{50}$ values: 320 nM vs 57 nM) although these two compounds showed similar activity in peripheral blood mononuclear cells ($IC_{50}$ values: 33 nM vs 42 nM). Thus, the identity of the para-substituent appears to affect the anti-HIV activity of the aryl phosphate derivatives of d4T in TK-deficient cells. To our knowledge, this is the first demonstration that the potency as well as the selectivity index of the d4T-aryl-phosphate derivatives can be substantially enhanced by introducing a single para-bromo substituent in the aryl moiety. This previously unknown structure-activity relationship determined by the aryl moiety of the phosphate derivatives of d4T provides a basis for the design of potentially more potent d4T analogues.

Example 5

Activity of Compound 4 and AZT in MDR cells

The activity of compound 4 (d4T-5'-[p-bromophenyl methoxyalaninyl phosphate]) against HIV-MDR cells was compared with AZT-5'-[p-bromophenyl methoxyalaninyl phosphate] (P-AZT) and with AZT. The incubation and analysis methods used were as described above for Example 3.

As shown in Table 2, P-AZT and AZT have similar activities with the $IC_{50}$ values of 1.5 and 2.0 nM, respectively. The activity of Compound 4 (0.02 nM) is 100-fold more effective than AZT (2.0 nM).

TABLE 2

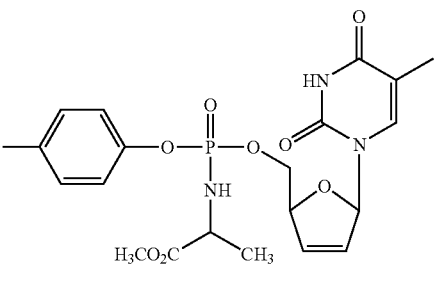

4

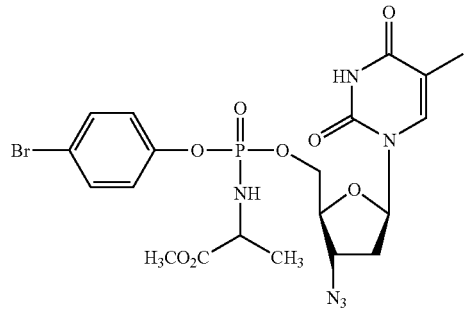

P-AZT

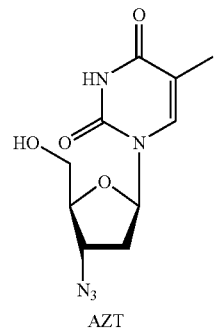

AZT

| Compound | HIV-2 $IC_{50}$ [RT] | HIV-MDR $IC_{50}$ [RT] |
|---|---|---|
| 4 | 0.4 | 0.02 |
| P-AZT | 3.9 | 1.5 |
| AZT | 2.4 | 2.0 |

Example 6

Synthesis of Arylphosphate Derivatives of 3dT

By way of further comparison, the effect on anti-HIV activity of various substitutions in the aryl group of arylphosphate derivatives of 3'-deoxytbymidine (3dT) was studied. As shown in Scheme 2, 3dt 5 was prepared from d4T 1 which was prepared from thymidine using the literature procedure (Mansuri et al., 1989, *J.Med.Chem.*, 32:461–466). Hydrogenation of 1 was carried out in ethanol in the presence of $H_2$ and catalytic amount of 5% Pd/C to afford 3dT 5 in 85% yield. Appropriately substituted phenyl methoxyalaninyl phosphorochloridates were also prepared according to the method reported by McGuigan et.al., 1992, *Antiviral Res*, 17:311–321, and compounds 6–11 were synthesized as outlined in Scheme 2.

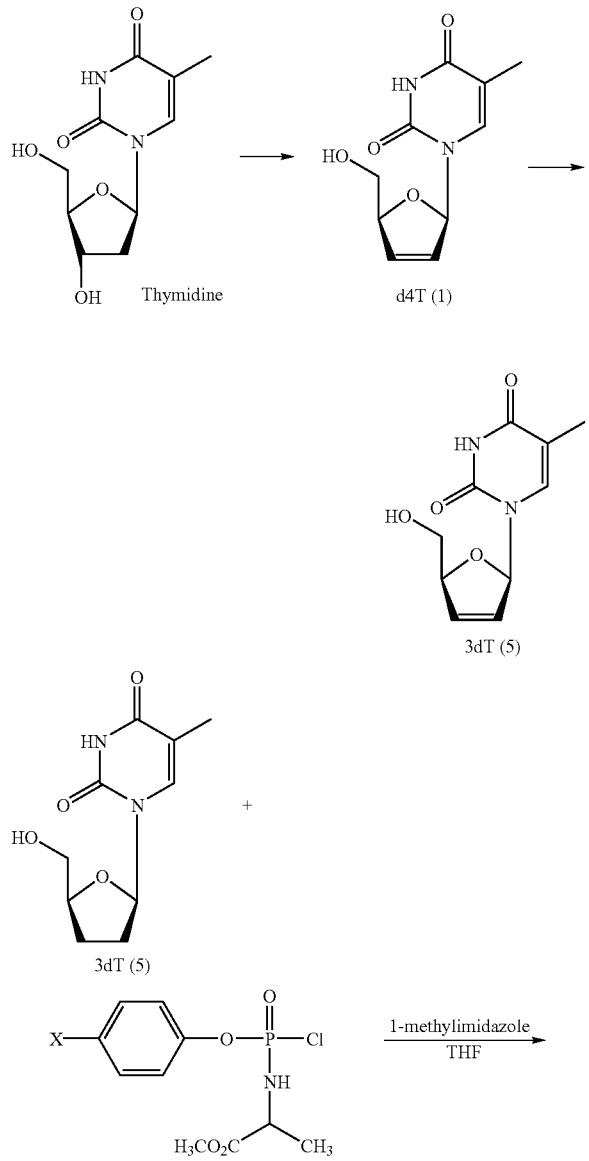

Scheme 2.

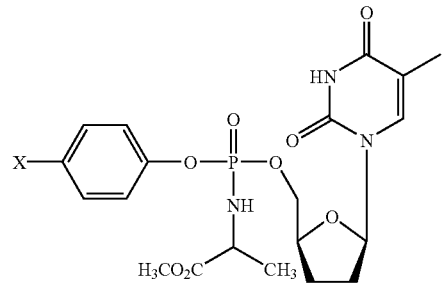

6: X = H
7: X = Cl
8: X = F
9: X = Br
10: X = $NO_2$
11: X = $OCH_2$

The appropriately substituted phenyl methoxyalaninyl phosphorochloridate was added to a mixture of 3dT and 1-methylimidazole in anhydrous THF. The reaction mixture were stirred for 12 h at room temperature and then solvent was removed. The resulting gum was re-dissolved in chloroform and washed with 1M HCl, saturated sodium bicarbonate solution (except in the case of the $NO_2$ derivative) and then with water. The organic phase was dried by $MgSO_4$ and the solvent was removed in vacuo. The crude product was purified by silica gel flash column chromatography eluted with 5% methanol in chloroform to give pure compounds 6–11 in good yields.

Physical data of the synthesized compounds was determined. HPLC was conducted using C18 4×250 mm LiChrospher column eluted with 70:30 water/acetonitrile at the flow rate of 1 ml/minute. The purity of the following compounds exceed 96% by HPLC. $^{13}C$ NMR peaks labeled by stars are split due to diastereomers. Physical data for the compounds is shown below.

Compound 5: yield: 85%; $^1H$ NMR($CDCl_3$) δ 11.1 (br s, 1H), 7.82 (s, 1H), 5.97–5.94 (m, 1H), 5.10 (br s, 1H), 4.05–3.95 (m, 1H), 3.72–3.52 (m, 2H), 2.30–1.86 (m, 4H), 1.77 (s, 3H); $^{13}C$ NMR($CDCl_3$) δ 163.9, 150.4, 136.4, 108.7, 84.8, 81.4, 62.2, 31.8, 25.1, and 12.5.

Compound 6: yield: 96%; IR (neat): 3211, 2955, 2821, 1689, 1491, 1265, 1211, 1153, 1043 and 933 $cm^{-1}$; $^1H$ NMR($CDCl_3$) δ 10.1 (br s, 1H), 7.47 (s, 1H), 7.32–7.12 (m, 5H), 6.14–6.08 (m, 1H), 4.41–4.21 (m, 4H), 4.05–4.00 (m, 1H), 3.70, 3.69 (s, 3H), 2.37–2.32 (m, 1H), 2.05–1.89 (m, 7H), 1.38–1.35 (dd, 3H); $^{13}C$ NMR($CDCl_3$) δ 173.6*, 163.8, 150.3, 150.1*, 135.2, 129.4*, 124.7, 119.8*, 110.5*, 85.7*, 78.3*, 67.2*, 52.3, 50.1*, 31.6*, 25.4*, 20.7*, and 12.4*; $^{31}P$ NMR($CDCl_3$) δ 2.82 & 3.11; MS (MALDI-TOF): 490.4 (M+Na); HPLC retention time=6.86, 7.35 minutes.

Compound 7: yield: 96%; IR (neat): 3217, 2954, 2821, 1743, 1689, 1489, 1265, 1217, 1153, 1092, 1012, 926 & 837 $cm^{-1}$; $^1H$ NMR($CDCl_3$) δ 9.40 (br s, 1H), 7.43–7.41 (m, 1H), 7.30–7.14 (m, 4H), 6.13–6.07 (m, 1H), 4.39–4.00 (m, 5H), 3.71, 3.70 (s, 3H), 2.38–2.36 (m, 2H), 2.09–1.89 (m, 5H), 1.39–1.36 (dd, 3H); $^{13}C$ NMR($CDCl_3$) δ 173.6*, 163.7, 150.2, 148.8*, 135.3, 129.5–129.0, 121.5–121.3, 116.3, 110.6, 86.0*, 78.4*, 67.7*, 52.6*, 50.2*, 31.8*, 25.4*, 20.9* and 12.5; $^{31}P$ NMR($CDCl_3$) δ 2.87 & 3.09; MS (MALDI-TOF): 524.9 (M+Na); HPLC retention time=14.05, 14.89 minutes.

Compound 8: Viscous oil, yield: 96%; $\lambda_{max}$: 223 (ε3338) and 269 (ε4695) nm; IR (neat): 3211, 2955, 1743, 1693, 1500, 1569, 1265, 1197, 1153, 1045, 923 & 843 cm$^{-1}$; $^1$H NMR(CDCl$_3$) δ 9.40 (br s, 1H), 7.45–7.43 (d, 1H), 7.19–7.01 (m, 4H), 6.14–6.06 (m, 1H), 4.39–3.97 (m, 5H), 3.71, 3.70 (s, 3H), 2.38–1.89 (m, 7H), 1.39–1.35 (t, 3H); $^{13}$C NMR(CDCl$_3$) δ 173.6*, 163.7, 150.2, 150.1*, 135.3, 121.5*, 116.3*, 110.6*, 85.9*, 78.4*, 67.7*, 52.6, 50.2*, 31.8*, 25.6*, 20.9*, and 12.5; $^{31}$P NMR(CDCl$_3$) δ 3.13 & 3.37; MS (MALDI-TOF): 508.2 (M+Na); HPLC retention time=8.38, 8.80 minutes.

Compound 9: yield: 83%; IR (neat): 3211, 2954, 1743, 1689, 1485, 1265, 1217, 1153, 1010, 923 & 833 cm$^{-1}$; $^1$H NMR(CDCl$_3$) δ 9.82 (br s, 1H), 7.45–7.41 (m, 3H), 7.15–7.11 (m, 2H), 6.14–6.06 (m, 1H), 4.39–4.00 (m, 5H), 3.71, 3.70 (s, 3H), 2.38–1.89 (m, 7H), 1.39–1.35 (dd, 3H); $^{13}$C NMR(CDCl$_3$) δ 173.6*, 163.8, 150.3, 148.5*, 135.2, 132.6*, 121.8*, 117.7, 110.6*, 85.9*, 78.3*, 67.2*, 52.5, 50.2*, 31.6*, 25.6*, 20.8*, and 12.5; $^{31}$P NMR(CDCl$_3$) δ 2.83 & 3.05; MS (MALDI-TOF): 570.0 (M+2+Na); HPLC retention time=15.50, 16.57 minutes.

Compound 10: yield, 87%; IR (neat): 3203, 2955, 1743, 1684, 1593, 1522, 1348, 1265, 1153, 1101, 920 & 860 cm$^{-1}$; $^1$H NMR(CDCl$_3$) δ 9.51 (br s, 1H), 8.24–8.21 (m, 2H), 7.42–7.37 (m, 3H), 6.13–6.08 (m, 1H), 4.39–4.03 (m, 5H), 3.72, 3.71 (s, 3H), 2.38–1.89 (m, 7H), 1.41–1.38 (dd, 3H); $^{13}$C NMR(CDCl$_3$) δ 173.4*, 163.7, 155.2*, 150.2, 144.4, 135.3, 125.9–125.4, 120.6*, 115.4, 110.6*, 86.1*, 78.4*, 68.1*, 52.7, 50.2*, 31.7*, 25.8*, 20.9* and 12.5; $^{31}$P NMR (CDCl$_3$) δ 2.60 & 2.81; MS (MALDI-TOF): 535.0 (M+Na); HPLC retention time=8.12, 10.14 minutes.

Compound 11: yield: 100%; IR (neat): 3209, 2954, 1743, 1506, 1468, 1265, 1207, 1153, 1036, 937 & 835 cm$^{-1}$; $^1$H NMR(CDCl$_3$) δ 9.89 (br s, 1H), 7.49–7.47 (m, 1H), 7.16–7.11 (m, 2H), 6.84–6.80 (m, 2H), 6.15–6.09 (m, 111H), 4.39–4.02 (m, 5H), 3.77, 3.76 (s, 3H), 3.74, 3.73 (s, 3H), 2.38–1.89 (m, 7H), 1.38–1.33 (t, 3H); $^{13}$C NMR(CDCl$_3$) δ 173.7*, 163.9, 156.3, 143.7*, 135.2, 120.7*, 114.3*, 110.5, 85.7*, 78.4*, 67.3*, 55.4, 52.4, 50.1*, 31.8*, 25.4*, 20.8* and 12.4*; $^{31}$P NMR(CDCl$_3$) δ 3.27 & 3.52; MS (MALDI-TOF): 521.3 (M+1+Na); HPLC retention time=7.15, 7.66 minutes.

Example 7

Antiviral Activity of 3dT Compounds 6–11

Compounds 6–11 as well as the parent compound 3dT were tested in side-by-side comparison with d4T for their ability to inhibit HIV-1 replication in peripheral blood mononuclear cells and TK-deficient CEM T-cells using previously described procedures (Zarling et.al., 1990, Nature, 347:92; Erice et al., 1993, Antimicrob. Agents Chemother., 37(4):835–838; Uckun et al., 1998, Supra).

3dT as well as its derivatives were less active than d4T in peripheral blood mononuclear cells as well as TK-deficient CEM T-cells (Table 3). Notably, in peripheral blood mononucleare cells, the IC$_{50}$[RT] values for compounds 6–11 were higher than the IC$_{50}$[RT] value of 3dT (1.2–3.1 versus 0.7, Table 3), suggesting that these prodrugs are sufficiently stable and TK-independent steps in their metabolism, perhaps their enzymatic hydrolysis, may be rate-limiting for generation of active species. In contrast, aryl phospate derivatives of d4T were reported to be more potent than d4T suggesting that the TK-dependent generation of d4T monophospate is rate-limiting in its metabolic activation (McGuigan et al., 1996, Bioorg. Med. Chem. Lett., 6:1183–1186). In accordance with the reported results in the literature regarding the biologic activity of aryl phospate derivatives of d4T and AZT, the aryl phosphate derivatives of 3dT were more active than the parent compound 3dT in inhibiting HIV-1 replication in TK-deficient cells, albeit with still high micromolar IC$_{50}$[RT] values (Table 3).

Since compounds 6–11 were less active in TK-deficient CEM T-cells than they were in peripheral blood mononuclear cells (PBMNC), it was postulated that the conversion of 3dT monophosphate generated from these prodrugs into its active triphosphate occurs at a much slower rate in the absence of TK. By comparison, the aryl phospate derivatives of d4T showed similar activity in normal and TK-deficient cells (McGuigan et al., 1996, Bioorg.Med.Chem. Lett. 6:1183–1186).

Anti-HIV Activity of aryl phosphate derivatives of 3'-deoxythymidine (6–11) in normal peripheral blood mononuclear cells (PBMNC) and TK-deficient CEM T-cells. All data are in μM and represent concentrations required to inhibit viral replication, as measured by RT activity, by 50% (IC$_{50}$ [RT])$^9$ or the 50% cytotoxic concentration, as measured by MTA(IC$_{50}$[MTA])(Mansuri et.al., 1989, J. Med. Chem,. 32:461).

TABLE 3

| | | PBMNC | | CEM | |
|---|---|---|---|---|---|
| Compound | X | IC$_{50}$ [RT] | IC$_{50}$ [MTA] | IC$_{50}$ [RT] | IC$_{50}$ [MTA] |
| 6 | H | 2.1 | >100 | 7.5 | >100 |
| 7 | Cl | 2.1 | >100 | 21.9 | >100 |
| 8 | F | 3.1 | >100 | 32.7 | >100 |
| 9 | Br | 1.2 | >100 | 22.8 | >100 |
| 10 | NO$_2$ | 2.0 | >100 | 22.6 | >100 |
| 11 | OMe | 1.3 | >100 | 19.7 | >100 |
| 3dT | — | 0.7 | >100 | 91.2 | >100 |
| d4T | — | 0.004 | >100 | 2.335 | >100 |

As shown in FIGS. 5A and 5B, the electronic effect of the para substitutions in the phenyl ring should affect the hydrolytic conversion of B to D in the metabolic pathway of aryl phosopate derivatives of 3dT depicted in FIG. 1. The presence of an electron-withdrawing substituent at the para position of the phenyl moiety was expected to increase the hydrolysis rates of the substituted phenoxy groups in compounds 7–10 (FIGS. 2A and 2B). However, these compounds were not more active than compound 6 with no para substitution or compound 11 with an electron donating para substituent, prompting the hypothesis that the carboxyesterase-dependent first hydrolysis step in their metabolism (A to B in FIG. 1) plays a critical and rate-limiting role for the generation of active 3dT metabolites. Thus, compounds 7–10 may serve as relatively poor substrates for the putative carboxyesterase responsible for their hydrolysis according to metabolic pathway proposed for aryl methoxyalaninyl phosphate derivatives of nucleoside analogs (McIntee et al., 1997, J.Med.Chem. 40:3323–3331).

In summary, the aryl phospate derivative of 3dT did not behave as what might have been expected from published work regarding the metabolism and activity of the prodrug forms of a very similar nucleoside analog, d4T. Surprisingly, the aryl phospate derivatives of 3dT did not elicit promising anti-HIV activity in HIV-1 infected normal peripheral blood mononuclear cells or TK-deficient CEM T-cell line.

Example 8

Anti-HIV Activity of Derivatives of d4T, AZT, and 3dT

As shown in Scheme 3, d4T 1 was prepared from thymidine using the literature procedure (Mansuri et.al., 1989, Supra). Hydrogenation of 1 in ethanol in the presence of $H_2$ and catalytic amount of 5% Pd/C afforded 3dT 3 in 85% yield (Scheme 3).

AZT 2 was prepared from thymidine using the literature methods (Chu et.al., U.S. Pat. No. 4,841,039). The ddN phosphorylation agents possessing different substituents in their phenoxy moieties 5a, 5b and 5c were prepared from the commercially available phenols in two-step procedures (Scheme 4) (McGuigan et.al., 1992, Supra),where Compounds 4a, 4b, 5a, 5b, 7a and 7b were previously reported. Compounds 4c and 5c are novel and their synthetic procedures as well as characterization data are reported below.

The synthesis of phenyl methoxyalaninyl phosphate derivatives of d4T 1, AZT 2 or 3dT 3 was carried out by following the literature condition as shown in Scheme 5 (McGuigan et.al., 1992, *Antiviral Res*, 17:311–321). The general synthetic procedures are as follows: The appropriately substituted phenyl methoxyalaninyl phosphorochloridate 5 was added to a mixture of the desired ddN (1, 2 or 3) and 1-methylimidazole in anhydrous THF. The reaction mixture were stirred for 12 hours at room temperature and then solvent was removed. The resulting gum was re-dissolved in chloroform and washed with 1M HCl, saturated sodium bicarbonate solution and then with water. The organic phase was dried by $MgSO_4$ and the solvent was removed in vacuo. The crude product was purified by silica gel flash column chromatography using a solvent mixture of methanol and chloroform for elution to give the desired pure compounds in good yields.

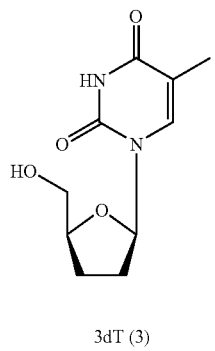

3dT (3)

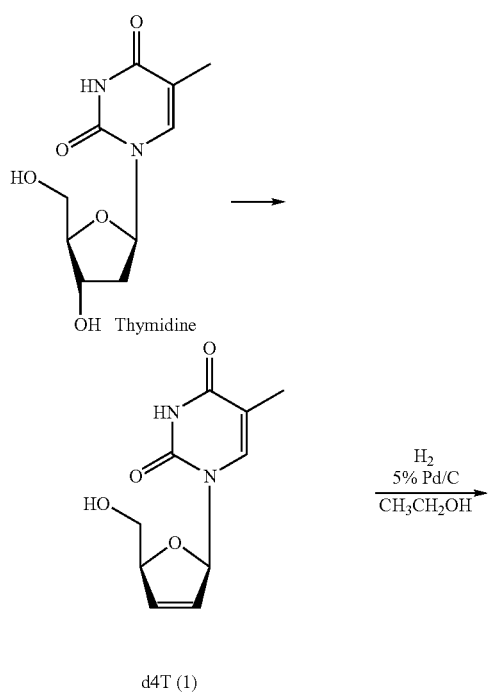

Scheme 3. Synthesis of d4T and d3T

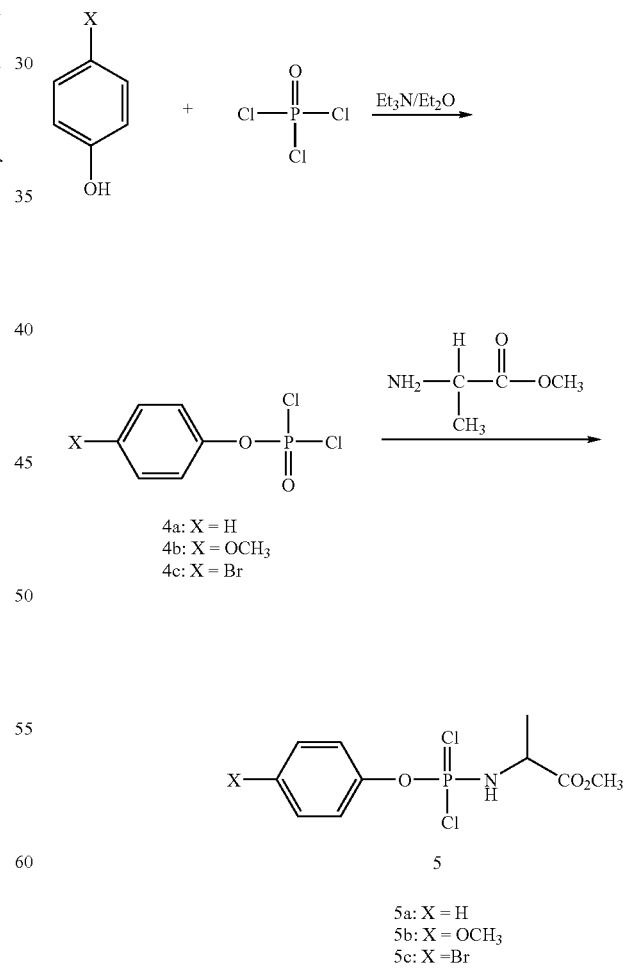

Scheme 4. Synthesis of phenyl methoxyalaninyl phosphorochloridates

Scheme 5: Synthesis of phenyl methoxyalaninyl phosphate derivatives of ddN

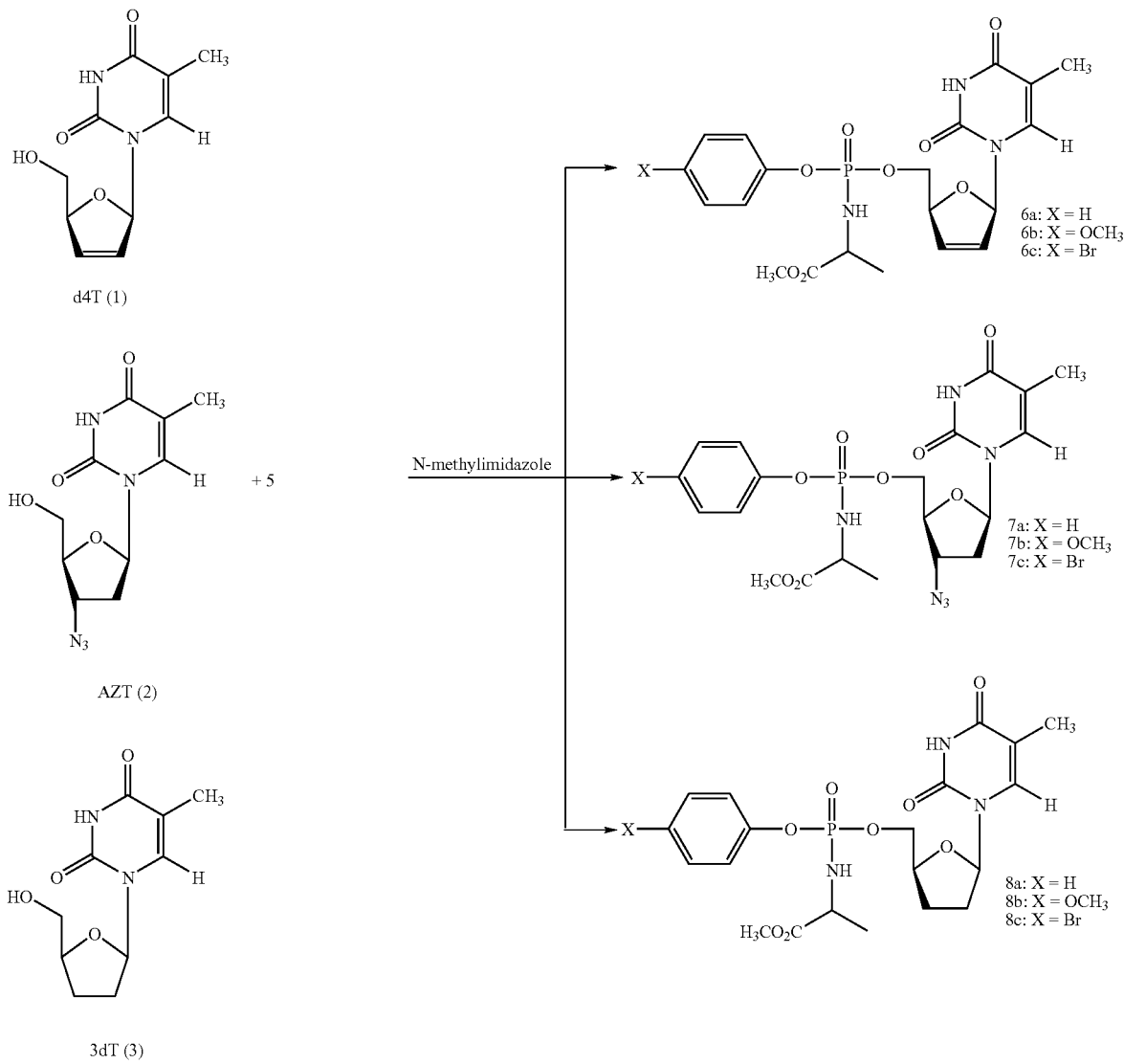

Synthesis of p-Bromophenyl phosphorodichloridate 4c. Following the procedure described by McGuigan et al., 1993, Supra, a solution of p-bromophenol (13.20 g; 76.30 mmol) and distilled triethylamine (10.65 mL) in anhydrous Et$_2$O (165 mL) was added dropwise into a vigorously stirred solution of phosphoryl chloride (8.5 mL; 91.2 mmol) in anhydrous Et$_2$O (83 mL) at 0° C. over a period of three hours under nitrogen atmosphere. Subsequently, the resultant mixture was gradually warmed up to room temperature, stirred efficiently overnight at room temperature and then heated to reflux for two hours. The reaction mixture was cooled to room temperature and filtered under aspirator pressure. The precipitate was washed with anhydrous Et$_2$O (2×50 mL). The combined Et$_2$O layers were evaporated to dryness on rotary evaporator to yield crude 4c as a pale yellow oil which was then subjected to vacuum distillation to give pure 4c (14.05 g; 63.5% yield) as a colorless viscous oil (bp. 110–115° C./2 mm Hg). IR (Neat) 3095, 1481, 1303, 1187, 948, 829 cm$^{-1}$. $^1$H NMR (300 MHz, CDCl$_3$) δ 7.50 (2H, d, J=9.0 Hz), 7.15 (2H, d, J=9.0 Hz). GC/MS (m/e) 290 (M$^+$), 254 (M$^+$-Cl), 173 (M$^+$-POCl$_2$, $^{81}$Br), 171 (M$^+$-POCl$_2$, $^{79}$Br), 156 (M$^+$-PO$_2$Cl$_2$, $^{81}$Br), 154 (M$^+$-PO$_2$Cl$_2$, $^{79}$Br).

Synthesis of p-Bromophenyl methoxyalaninyl phosphorochloridate 5c. Following the procedure described by (McGuigan et.al., 1992, Antiviral Res, 17:311–321), a solution of distilled triethylamine (8.80 mL; 63.14 mmol) in anhydrous CH$_2$Cl$_2$ (180 mL) was added dropwise via an addition funnel into a vigorously stirred solution of p-bromophenyl phosphorodichloridate 4c (8.69 g; 29.97 mmol) and L-alanine methyl ester hydrochloride (4.19 g; 30.02 mmol) in anhydrous CH$_2$Cl$_2$ (250 mL) at −70° C. over a period of three hours under nitrogen atmosphere. Subsequently, the resultant mixture was allowed to gradually warm up to room temperature and stirred overnight at room temperature. The solvent was removed on rotary evaporator. Anhydrous Et$_2$O (300 mL) was added to dissolve the residue and then filtered under aspirator pressure to remove the white solid. The white solid was rinsed with anhydrous Et$_2$O (2×60 mL). The Et$_2$O layers were combined and evaporated to dryness to afford a quantitative yield of 5c (10.7 g) as a pale pink-yellow viscous oil. This product was then used for the next step reaction without further purification. IR (Neat) 3212, 2989, 2952, 1747, 1483, 1270, 1209, 1147, 927, 831, 757 cm$^{-1}$. $^1$H NMR (300 MHz, CDCl$_3$) δ 8.70 (1H, br, Ala-NH), 7.48 (2H, d, J=9.0 Hz, aryl H), 7.16 (2H, d, J=9.0 Hz, aryl H), 3.79 & 3.77 (3H, s & s, —OCH$_3$), 1.51 & 1.40 (3H, d & d, Ala-CH$_3$). MS (CI, m/e) 357.9 (M$^+$, $^{81}$Br), 355.9 (M$^+$, $^{79}$Br), 322.0 (M$^+$-Cl, $^{81}$Br), 320.0 (M$^+$-Cl, $^{79}$Br), 297.9 (M$^+$-COOCH$_3$, $^{81}$Br), 295.9 (M$^+$-COOCH$_3$, $^{79}$Br), 184.0 (M$^+$BrC$_6$H$_4$O).

Characterization data of phenyl methoxyalaninyl phosphate derivatives of AZT 1, d4T 2 and 3dT 3: HPLC was conducted by using C18 4×250 mm LiChrospher column eluted with 70:30 water/acetonitrile at the flow rate of 1 ml/minute. The purity of the following compounds exceed 96% by HPLC. $^{13}$C NMR peaks labeled by asterisks were split due to diastereomers arising from the phosphorus stereocenters.

Characterization data of Compound 6a: yield: 81%; IR (Neat): 3222, 2985, 2954, 1743, 1693, 1593, 1491, 1456, 1213, 1153, 1039, 931, 769 cm$^{-1}$; $^1$H NMR (CDCl$_3$) δ 9.30 (br s, 1H), 7.30–7.10 (m, 6H), 6.85–6.82 (m, 1H), 6.36–6.26 (m, 1H), 5.91–5.85 (m, 1H), 5.00 (br m, 1H), 4.19–3.68 (m, 4H), 3.72, 3.71 (s, 3H), 1.83, 1.80 (d, 3H), 1.38–1.25 (m, 3H); $^{13}$C NMR(CDCl$_3$) δ 173.9, 163.7, 150.7, 149.7, 135.7*, 133.2*, 129.6*, 127.3*, 125.0*, 120.0, 111.1, 89.6*, 84.5*, 66.9*, 52.5*, 50.0*, 20.9 and 12.3; $^{31}$P NMR(CDCl$_3$) δ 2.66, 3.20; MALDI-TOF mass m/e 487.9 (M+Na); HPLC retention time: 5.54 & 5.85 minute.

Characterization data of Compound 6b: yield: 92%; IR (Neat): 3223, 3072, 2999, 2953, 2837, 1743, 1693, 1506, 1443, 1207, 1153, 1111, 1034, 937, 837 and 756 cm$^{-1}$; $^1$H NMR(CDCl$_3$) δ 9.40 (br s, 1H), 7.30–7.00 (m, 5H), 6.83–6.81 (m, 1H), 6.37–6.27 (m, 1H), 5.91–5.86 (m, 1H), 5.00 (br m, 1H), 4.40–4.30 (m, 2H), 4.20–4.10 (m, 2H), 3.95–3.93 (s, 3H), 3.82–3.80 (s, 3H), 1.85–1.81 (s, 3H) and 1.39–1.29 (m, 3H); $^{13}$C NMR(CDCl$_3$ ) δ 174.0, 163.9, 156.6, 150.8, 143.5, 135.8*, 133.3*, 127.4*, 121.2*, 114.5, 111.2, 89.7*, 84.5, 66.9*, 55.5, 52.5, 50.6*, 20.9, and 12.3; $^{31}$P NMR(CDCl$_3$) δ 3.82, 3.20; MALDI-TOF mass m/e 518.2 (M+Na); HPLC retention time: 5.83 & 6.26 minute.

Characterization data of Compound 6c: yield: 83%; IR (Neat): 3203, 3070, 2954, 2887, 2248, 1743, 1693, 1485, 1221, 1153, 1038, 912, 835, 733 cm$^{-1}$; $^1$H NMR(CDCl$_3$) δ 9.60–9.58 (br s, 1H), 7.45–7.42 (m, 2H), 7.30–7.09 (m, 4H), 6.37–6.27 (m, 1H), 5.93–5.88 (m, 1H), 5.04–5.01 (br m, 1H), 4.35–4.33 (m, 2H), 4.27–3.98 (m, 2H), 3.71–3.70 (s, 3H), 1.85–1.81 (s, 3H), 1.37–1.31 (m, 3H); $^{13}$C NMR (CDCl$_3$) δ 173.7, 163.8, 150.8, 149.7*, 135.6*, 133.1*, 127.4*, 121.9*, 118.0, 111.2*, 89.7*, 84.4*, 67.8*, 52.5, 50.0*, 20.7, and 12.3; $^{31}$P NMR(CDCl$_3$) δ 3.41, 2.78; MALDI-TOF mass m/e 567.1 (M+Na); HPLC retention time: 12.04 & 12.72 minute.

Characterization data of Compound 7c: yield: 95%; IR (Neat) 3205.7, 3066.3, 2954.5. 2109.8, 1745.3, 1691.3, 1484.9, 1270.9, 1153.2, 1010.5 and 926.1 cm$^{-1}$. $^1$H NMR (300 MHz, CDCl$_3$) δ 8.69 (1H, br, 3-NH), 7.45 (2H, d, J=9.0 Hz, aryl H), 7.34 & 7.32 (1H, s & s, vinyl H), 7.11 (2H, d, J=9.0 Hz, aryl H), 6.18 & 6.13 (1H, t & t, J=6.6 & 6.6 Hz, H at C-1'), 4.44–3.77 (6H, m, H at C-3', 4' & 5', Ala-NH and Ala-CH), 3.73 & 3.72 (3H, s & s, —COOCH$_3$), 2.51–2.20 (2H, m, H at C-2'), 2.18 (3H, s, —CH$_3$ at C-5), 1.39 & 1.36 (3H, d & d, Ala-CH$_3$). $^{13}$C NMR (75 MHz, CDCl$_3$) δ 173.6, 163.6, 150.1, 149.2, 149.1, 135.2, 132.4, 121.6, 117.8, 111.1, 85.0, 84.7, 81.9, 81.8, 65.5, 60.1, 59.9, 52.4, 50.0, 49.9, 36.9, 20.6, 20.5, 12.2. MS (CI, m/e) 589.1 (M$^+$, $^{81}$Br) and 587.1 (M$^+$, $^{79}$Br).

Characterization data of Compound 8a: yield: 96%; IR (Neat): 3211, 2955, 2821, 1689, 1491, 1265, 1211, 1153, 1043 and 933 cm$^{-1}$; $^1$H NMR(CDCl$_3$) δ 10.1 (br s, 1H), 7.47 (s, 1H), 7.32–7.12 (m, 5H), 6.14–6.08 (m, 1H), 4.41–4.21 (m, 4H), 4.05–4.00 (m, 1H), 3.70, 3.69 (s, 3H), 2.37–2.32 (m, 1H), 2.05–1.89 (m, 7H), 1.38–1.35 (dd, 3H); $^{13}$C NMR (CDCl$_3$) δ 173.6*, 163.8, 150.3, 150.1*, 135.2, 129.4*, 124.7, 119.8*, 110.5*, 85.7*, 78.3*, 67.2*, 52.3, 50.1*, 31.6*, 25.4*, 20.7*, and 12.4*; $^{31}$P NMR(CDCl$_3$) δ 2.82 & 3.11; MS (MALDI-TOF): 490.4 (M+Na); HPLC retention time=6.86, 7.35 minute.

Characterization data of Compound 8b: yield, 100%; IR (Neat): 3209, 2954, 1743, 1506, 1468, 1265, 1207, 1153, 1036, 937 & 835 cm$^{-1}$; $^1$H NMR(CDCl$_3$) δ 9.89 (br s, 1H), 7.49–7.47 (m, 1H), 7.16–7.11 (m, 2H), 6.84–6.80 (m, 2H), 6.15–6.09 (m, 1H), 4.39–4.02 (m, 5H), 3.77, 3.76 (s, 3H), 3.74, 3.73 (s, 3H), 2.38–1.89 (m, 7H), 1.38–1.33 (t, 3H); $^{13}$C NMR(CDCl$_3$) δ 173.7*, 163.9, 156.3, 150.3, 143.7*, 135.2, 120.7*, 114.3*, 110.5, 85.7*, 78.4*, 67.3*, 55.4, 52.4, 50.1*, 31.8*, 25.4*, 20.8* and 12.4*; $^{31}$P NMR(CDCl$_3$) δ 3.27 & 3.52; MS (MALDI-TOF): 521.3 (M+1+Na); HPLC retention time=7.15, 7.66 minute.

Characterization data of Compound 8c: yield: 83%; IR (Neat): 3211, 2954, 1743, 1689, 1485, 1265, 1217, 1153, 1010, 923 & 833 cm$^{-1}$; $^1$H NMR(CDCl$_3$) δ 9.82 (br s, 1H), 7.45–7.41 (m, 3H), 7.15–7.11 (m, 2H), 6.14–6.06 (m, 1H), 4.39–4.00 (m, 5H), 3.71, 3.70 (s, 3H), 2.38–1.89 (m, 7H), 1.39–1.35 (dd, 3H); $^{13}$C NMR(CDCl$_3$) δ 173.6*, 163.8, 150.3, 148.5*, 135.2, 132.6*, 121.8*, 117.7, 110.6*, 85.9*, 78.3*, 67.2*, 52.5, 50.2*, 31.6*, 25.6*, 20.8*, and 12.5; $^{31}$P NMR(CDCl$_3$) δ 2.83 & 3.05; MS (MALDI-TOF): 570.0 (M+2+Na); HPLC retention time=15.50, 16.57 minute.

Example 9

Anti-HIV Activity of Compounds 6a–8c

Cellular Assays of Anti-HIV Activity and Cytotoxicity. Anti-HIV activities were evaluated in AZT-sensitive HIV-1 (strain: HTLV$_{IIIB}$)-, AZT- and NNI-resistant HIV-1 (strain: RTMDR-1)- (kindly provided by Dr. Brendan Larder, NIH AIDS Research and Reference Reagent Program, DIV. AIDS, NIAID, NIH; cat. # 2529), or HIV-2 (Strain: CBL-20)-infected peripheral blood mononuclear cells (PBMNC) as well as HTLV$_{IIIB}$-infected TK-deficient CEM T-cells by determining the concentration of compound needed to inhibit viral replication by 50%, based on reverse transcriptase activity assays (IC$_{50}$ [RT]). Percent viral inhibition was calculated by comparing the RT activity values from the test substance-treated infected cells with RT values from untreated infected cells (i.e., virus controls). The 50% cytotoxic concentrations of the compounds (CC$_{50}$[MTA]) were measured by microculture tetrazolium assay (MTA), using 2,3-bis(2-methoxy-4-nitro-5-sulfophenyl)-5-[(phenylamino)-carbonyl]-2H-tetrazolium hydroxide (XTT) (Zarling et.al., 1990, *Nature,* 347:92; Erice et.al., 1993, *Antimicrob.Agents Chemother.,* 37:835–838, Uckun et.al., 1998, Supra).

Identification of d4T-5'-(para-bromophenyl methoxyalaninyl phosphate) and AZT-5'-(para-bromophenyl methoxyalaninyl phosphate) as potent anti-HIV agents. The d4T-phenyl phosphate derivatives were not more potent than the parent compound d4T when tested in HIV-1-infected PBMNC. The ability of d4T to inhibit HIV-1 replication was substantially reduced in TK-deficient CEM cells. Whereas the $IC_{50}$ value for inhibition of the RT activity by d4T was 40 nM in PBMNC, it was 2400 nM in TK-deficient CEM cells (Table 4 & FIGS. 4A–4F). While all three phenyl phosphate derivatives were more potent than d4T in TK-deficient CEM cells, compound 6c (d4T-5'-[p-bromo phenylmethoxyalaninyl phosphate]) with a para-bromo substituent in the phenyl moiety was 60-fold more potent in inhibiting the RT activity ($IC_{50}$ values: 60 nM vs 2400 nM) than d4T (Table 4).

None of the compounds exhibited any detectable cytotoxicity to PBMNC or CEM cells at concentrations as high as 10,000 nM, as determined by MTA. Intriguingly, compound 6b with a para-methoxy substituent in the phenyl moiety was 5-fold less effective than compound 6c in inhibiting the RT activity in HIV-infected TK-deficient CEM cells ($IC_{50}$ values: 300 nM vs 60 nM) although these two compounds showed similar activity in peripheral blood mononuclear cells ($IC_{50}$ values: 30 nM vs 40 nM) (Table 4).

Compounds 7a, 7b, 7c and their parent compound AZT 2 were tested for their ability to inhibit HIV replication in PBMNC and TK-deficient CEM T-cells (Table 4). Percent inhibition of viral replication was calculated by comparing the RT activity values from the test substance-treated infected cells with those from untreated infected cells. In parallel, the cytotoxicity of the compounds was examined using a microculture tetrazolium assay (MTA) of cell proliferation. The ability of AZT 2 to inhibit HIV-1 replication was substantially reduced in TK-deficient CEM cells. Whereas the $IC_{50}$ value for inhibition of RT activity by AZT was 3 nM in PBMNC, it was 200 nM in TK-deficient CEM cells. Unlike the corresponding d4T derivatives, the unsubstituted and para substituted phenyl phosphate derivatives of AZT were not more potent than the parent compound AZT when tested in HIV-1 infected TK-deficient CEM T-cells. However, the para-bromo substituted phenyl phosphate derivative of AZT, AZT-5'-(para-bromophenyl methoxyalaninyl phosphate) 7c, was 5 times more effective than AZT in inhibiting HIV replication of TK-deficient CEM cells ($IC_{50}$ [RT] values: 0.04 μM vs 0.2 μM). None of the compounds exhibited any detectable cytotoxicity to PBMNC or CEM cells at concentrations as high as 10,000 nM, as determined by MTA.

Compounds 8a–c and their parent compound 3dT 3 were tested in side-by-side comparison with d4T 1 for their ability to inhibit HIV-1 replication in PBMNC and TK-deficient CEM T-cells. 3dT as well as its derivatives were less active than d4T in peripheral blood mononuclear cells as well as TK-deficient CEM T-cells (Table 4). Notably, in peripheral blood mononuclear cells, the $IC_{50}$[RT] values for compounds 8a–c were higher than the $IC_{50}$[RT] value of 3dT (1.2–3.1 versus 0.7, Table 4), suggesting that these prodrugs are sufficiently stable and TK-independent steps in their metabolism, perhaps their enzymatic hydrolysis, may be rate-limiting for generation of active species. In accordance with the reported results in the literature regarding the biologic activity of phenyl phospate derivatives of d4T and AZT the phenyl phosphate derivatives of 3dT were more active than the parent compound 3dT in inhibiting HIV-1 replication in TK-deficient cells, albeit with still high micromolar $IC_{50}$[RT] values (Table 4 & FIGS. 4A–4F). Since compounds 8a–c were less active in TK-deficient CEM T-cells than they were in PBMNC, we postulate that the conversion of 3dT monophosphate generated from these prodrugs into its active triphosphate occurs at a much slower rate in the absence of TK.

TABLE 4

Anti-HIV Activity of phenyl methoxyalaninyl phosphate derivatives of d4T, AZT and 3dT in normal peripheral blood mononuclear cells (PBMNC) and TK-deficient CEM T-cells.

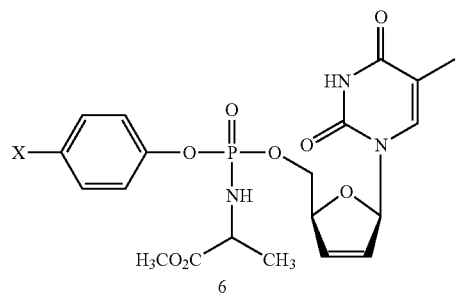

6

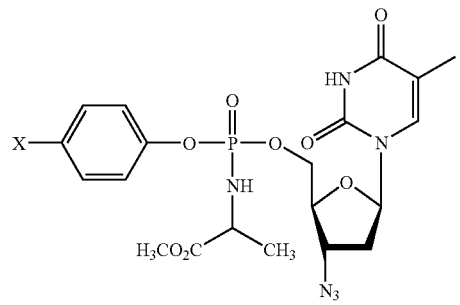

7

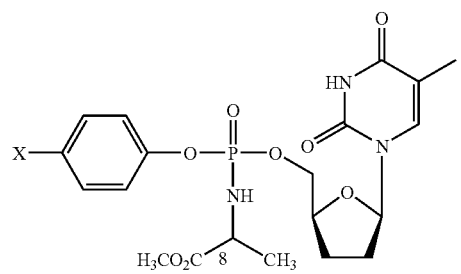

| | | PBMNC | | CEM | |
|---|---|---|---|---|---|
| Compound | X | IC$_{50}$ [RT] | IC$_{50}$ [MTA] | IC$_{50}$ [RT] | IC$_{50}$ [MTA] |
| 6a | H | N.D. | N.D. | 0.1 | >10 |
| 6b | OCH$_3$ | 0.03 | >10 | 0.3 | >10 |
| 6c | Br | 0.04 | >10 | 0.06 | >10 |
| 7a | H | N.D. | N.D. | 1.7 | >10 |
| 7b | OMe | 0.1 | >10 | 4.1 | >10 |
| 7c | Br | 0.004 | >10 | 0.04 | >10 |
| 8a | H | 2.1 | >10 | 7.5 | >10 |
| 8b | OMe | 1.3 | >10 | 19.7 | >10 |
| 8c | Br | 1.2 | >10 | 22.8 | >10 |
| 1 (d4T) | — | 0.04 | >10 | 2.4 | >10 |
| 2 (AZT) | — | 0.003 | >10 | 0.2 | >10 |
| 3 (3dT) | — | 0.7 | >10 | 91.2 | >10 |

Compounds 6a, 6b and 6c are all more potent than the parent d4T 1 in TK-deficient CEM cells, while these d4T-phenyl phosphate derivatives (6a, 6b and 6c) are not more potent than the parent d4T 1 in HIV-1 infected PBMNC (Table 4). Comparing all the phenyl methoxyalaninyl phosphate derivatized d4T, d4T-5'-[p-bromo phenylmethoxyalaninyl phosphate] 6c is the most potent anti-HIV agent in TK-deficient CEM cells. This observation could be attributed to the para-bromo substituent in the phenyl moiety of 6c which enhances the ability of its phosphorus to undergo hydrolysis due to the electron withdrawing property of the bromo substituent (FIG. 2) and results in generation of substantially higher quantities of the key metabolite d4T monophosphate in the TK-deficient CEM T-cells (McIntee et.al., 1997, J.Med. Chem. 40:3233–3331).

The potency of phenyl, methoxyphenyl and bromophenyl phosphate derivatives of AZT in TK-deficient CEM cells also followed the same trend as that of d4T derivatives, namely 7c (bromophenyl)>7a (phenyl)>7b (methoxyphenyl). However, among the three phenyl methoxyalaninyl phosphate derivatives of AZT (7a, 7b and 7c), only 7c showed higher potency than AZT in TK-deficient CEM cells (IC$_{50}$ values: 40 nM vs 200 nM). For phenyl methoxyalaninyl phosphate derivatives of 3dT (Table 4), the presence of an electron-withdrawing substituent at the para position of the phenyl moiety was expected to increase the hydrolysis rates of the substituted phenoxy group in compound 8c (e.g. B to C in FIG. 2). However, 8c was not more active than compound 8a with no para substitution or compound 8b with an electron donating para substituent, prompting the hypothesis that the carboxyesterase-dependent first hydrolysis step in their metabolism (e.g. A to B in FIG. 2) plays a critical and rate-limiting role for the generation of active 3dT metabolites. We postulate that compounds 8a, 8b and 8c may serve as relatively poor substrates for the putative carboxyesterase responsible for their hydrolysis according to metabolic pathway proposed for phenyl methoxyalaninyl phosphate derivatives of nucleoside analogs (FIG. 2). The aryl phospate derivatives of 3dT did not behave as what might have been expected from the published work regarding the metabolism and activiy of the prodrug forms of a very similar nucleoside analog, d4T. To much of our surprise, the aryl phospate derivatives of 3dT did not elicit promising anti-HIV activity in HIV-1 infected normal peripheral blood mononuclear cells or TK-deficient CEM T-cell line.

In summary, d4T-5'-[p-bromo-phenylmethoxyalaninyl phosphate] 6c and AZT-5'-[p-bromo-phenylmethoxyalaninyl phosphate] 7c were identified as active anti-HIV agents which potently inhibit HIV replication in TK-deficient CEM T-cells without any detectable cytotoxicity In contrast to these d4T and AZT derivatives, the corresponding 3dT derivative, 3dT-5'-(para-bromophenyl methoxyalaninyl phosphate), showed no significant anti-HIV activity in PBMNC or TK-deficient CEM T-cells. To our knowledge, this is the first comprehensive report of a previously unappreciated structure activity relationship determining the potency of phenyl phosphate derivatives of d4T and AZT. Further development of the lead compounds 6c and 7c may provide the basis for the design of effective HIV treatment strategies capable of inhibiting HIV replication in TK-deficient cells.

Example 10

Activity of D4-T Derivatives Against Different HIV Strains

This example compared the activity of 12 d4-T derivatives against various HIV strains.

All chemicals were purchased from Aldrich (Milwaukee, Wis.), with the exception of d4T which was synthesized in-house. All syntheses were performed under a nitrogen atmosphere. $^1$H, $^{13}$C, and $^{31}$P NMR were obtained on a Varian Mercury 300 instrument at ambient temperature in CDCl$_3$. FT-IR spectra were recorded on a Nicolet Protege 460 spectrometer. MALDI-TOF mass spectra were obtained by using a Finnigan MAT 95 system. UV spectra were recorded by using a Beckmann UV-VIS spectrophotometer (Model 3DU 74000) with a cell path length of 1 cm. HPLC purification was achieved by using a reverse-phase Lichrospher column (250×4 mm, Hewlett-Packard, RP-18, Cat #

79925) and an isocratic flow (1 ml/minute) consisting of water (70%) and acetonitrile (30%). The alkaline chemical hydrolysis was conducted at room temperature with sodium hydroxide (1 ml of 0.05N) and 3 ml of methanol solution containing 10 mg of the substrates in a Teflon lined reaction vial. The solution was stirred using a magnetic stirrer and an aliquot of the reaction mixture was injected into HPLC. The disappearance of the starting material was monitored as a function of time. The rate of uni-molecular reaction was obtained using first order rate equation. HPLC runs were done with varying interval of time and measuring the disappearance of the substrate peak with time.

In vitro Assays of Anti-HIV-1 Activity. Normal human peripheral blood mononuclear cells (PBMNC) from HIV-negative donors were cultured 72 hours in RPMI 1640 supplemented with 20% (v/v) heat-inactivated fetal bovine serum (FBS), 3% interleukin-2, 2 mM L-glutamine, 25 mM HEPES, 2 g/L $NaHCO_3$, 50 mg/mL gentamicin, and 4 mg/mL phytohemagglutinin prior to exposure to HIV-1 at a multiplicity of infection (MOI) of 0.1 during a 1 hour adsorption period at 37° C. in a humidified 5% $CO_2$ atmosphere. Subsequently, cells were cultured in 96-well microtiter plates (100 mL/well; $2\times10^6$ cells/mL) in the presence of various concentrations of d4T phosphoramidates and aliquots of culture supernatants were removed from the wells on the $7^{th}$ day after infection for p24 antigen assays, as previously described (Uckun et al., 1998, *Antimicrobial Agents and Chem.*, 42(2):383–388). The applied p24 enzyme immunoassay (EIA) was the unmodified kinetic assay commercially available from Coulter Corporation/Immunotech, Inc. (Westbrooke, Me.), which utilizes a murine mAb to HIV core protein coated onto microwell strips to which the antigen present in the test culture supernatant samples binds. Percent viral inhibition was calculated by comparing the p24 values from untreated infected cells (i.e., virus controls).

Partition Coefficients. The octanol/water partition coefficient was determined by the shake flask method. The phosphoramidate analogs were added to 2 ml of water and 2 ml of octanol in a glass vial. The mixture was shaken for 4 hours at room temperature. The two phases were carefully separated and filtered through a Millipore filter and analyzed by HPLC. The partition coefficient was calculated using the ratio of the area under the curve for octanol and water respectively.

Statistical Analysis. The $IC_{50}$ values were calculated from each set of triplicate wells using nonlinear regression modeling of the exponential form of the linearized equation. The average $IC_{50}$ values were log, transformed to homogenize the variances within each group. Unpaired t-tests were performed in order to test for differences between the mean $IC_{50}$ values for different compound groups. Hydrolysis rates were determined by fitting single exponential decay equations to the disappearance of the compound in alkali conditions. The $IC_{50}$ values of the compounds were correlated to the log transformed hydrolysis rate constants by fitting a linear model (JMP Software, SAS Institute Inc.). P-values less than 0.05 were deemed significant.

The target phosphoramidate derivatives of stavudine were synthesized according to Scheme 6.

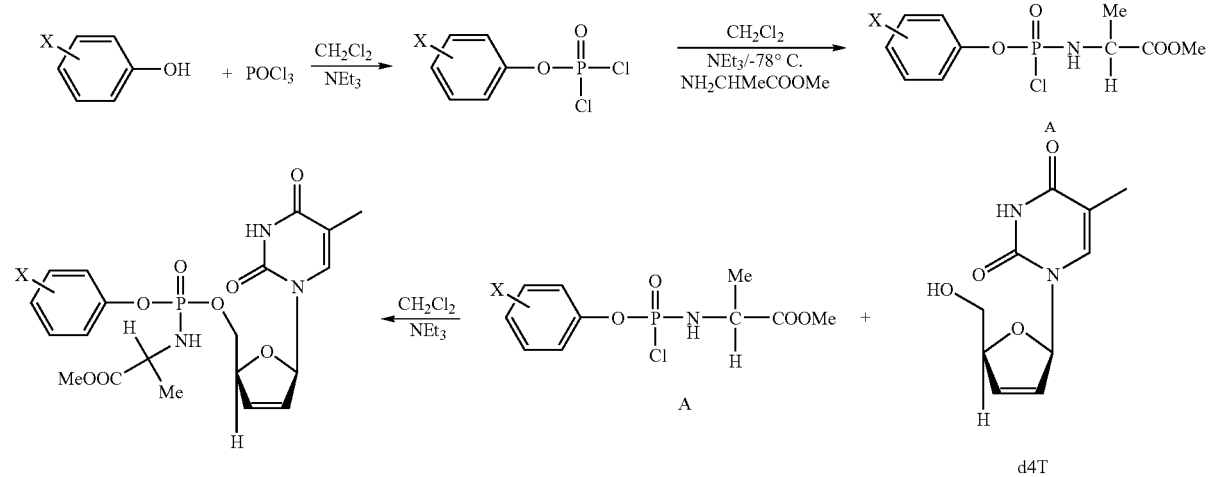

The characterization data of the synthesized compounds is given below.

5'-[3-Dimethylaminophenylmethoxyalaninylphosphate]-2',3'-didehydro-3'-deoxythymidine (DDE 599). Yield: 0.83 g (18%); mp: 61–62° C.; $^1$H NMR ($CDCl_3$) δ 9.93 (s, 1 H), 7.27 (br m, 1 H), 7.04 (m, 1 H), 6.97 (m, 1 H), 6.44 (m, 3 H), 6.24 (m, 1 H), 5.81 (m, 1 H), 4.94 (m, 1 H), 4.24 (s, 2 H), 4.08 (m, 1 H), 3.92 (m, 1 H), 3.64* (m, 3 H), 2.86 (s, 6 H), 1.77* (m, 3 H), 1.28* (m, 3 H); $^{13}$C NMR ($CDCl_3$) δ 173.7*, 163.9*, 151.3*, 150.8*, 135.5*, 132.9*, 129.5*, 126.9*, 111.0*, 108.8*, 107.2*, 103.7* 89.3*, 84.4*, 66.7*, 66.1*, 52.3*, 49.9*, 40.2, 20.7, 12.2; $^{31}$P NMR ($CDCl_3$) δ 3.32, 2.70; IR (KBr) ν 3448, 3050, 2952, 1691, 1506, 1450, 1247, 1143, 999 cm$^{-1}$; UV(MeOH) $\lambda_{max}$ 203, 206, 21, 258 nm; FAB MS m/z 531.1619 ($C_{22}H_{29}N_4O_8P+Na^+$); HPLC $t_R$ 3.36 min.

5'-[2,6-Dimethoxyphenylmethoxyalaninylphosphate]-2',3'-didehydro-3'-deoxythimidine (DDE 600). Yield: 0.60 g (13%); mp: 51–53° C.; $^1$H NMR ($CDCl_3$) δ 9.78 (s, 1 H), 7.38 (br d, 1 H), 6.95 (m, 3 H), 6.48 (m, 3 H), 6.29 (m, 1 H), 5.81 (m, 1 H), 4.36 (m, 3 H), 4.02 (m, 2 H), 3.74 (m, 6 H), 3.63* (m, 3 H), 1.74* (d, 3 H), 1.29* (m, 3 H); $^{13}$C NMR ($CDCl_3$) δ 173.7*, 163.9*, 151.7*, 150.8*, 135.7*, 133.1*, 128.4, 126.8*, 125.0*, 110.9*, 104.8*, 89.2, 84.6*, 66.8, 55.8*, 52.2*, 49.7*, 49.4*, 21.0*, 11.8*, $^{31}$P NMR (CDCl$_3$) δ 4.97, 4.28; IR (KBr) ν 3432, 3072, 2950, 1691, 1483, 1261, 1112, 931 cm$^{-1}$; UV(MeOH) λ$_{max}$ 210, 267 nm; FAB MS m/z 526.1570 (C$_{22}$H$_{28}$N$_3$O$_{10}$P+H$^+$); HPLC t$_R$ 6.55 min.

5'-[5'-[3-Bromophenylmethoxyalaninylphosphate]-2',3'-didehydro-3'deoxythymidine (DDE 602). Yield: 0.67 g (14%); mp: 47–48° C.; $^1$H NMR (CDCl$_3$) δ 9.65 (s, 1 H), 7.34–7.11 (m, 5 H), 6.97 (m, 1 H), 6.26 (m, 1 H), 5.87 (m, 1 H), 4.98 (m, 1 H), 4.26 (m, 3 H), 3.93 (m, 1 H), 3.67* (m, 3 H), 1.76* (m, 3 H), 1.32* (m, 3 H); $^{13}$C NMR (CDCl$_3$) δ 173.5*, 163.8*, 150.6*, 135.4, 132.8*, 130.6, 128.0, 127.3*, 123.3*, 122.3*, 118.8*, 111.1, 89.5*, 84.4*, 67.2, 66.6, 52.6, 50.0*, 20.7*, 12.3*, $^{31}$P NMR (CDCl$_3$) δ 3.36, 2.74; IR (KBr) ν 3432, 3070, 2954, 1685, 1473, 1247, 941 cm$^-$; UV(MeOH) λ$_{max}$ 208, 213, 267 nm; FAB MS m/z 544.0486 (C$_{20}$H$_{23}$BrN$_3$O$_8$P+H$^+$); HPLC t$_R$ 10.30, 10.65 min.

4-Bromo-2-chlorophenylmethoxyalaninylphosphate]-2',3'-didehydro-3'-deoxythymidine (DDE 603). Yield: 0.89 g (17%); mp: 51–52° C.; $^1$H NMR (CDCl$_3$) δ 9.52 (s, 1 H), 7.52 (s, 1 H), 7.32 (m, 2 H), 7.22 (m, 1 H), 6.99 (m, 1 H), 6.29 (m, 1 H), 5.90 (m, 1 H), 5.00 (m, 1 H), 4.33 (m, 2 H), 4.19 (m, 1 H), 4.01 (m, 1 H), 3.67 (s, 1 H), 1.79* (m, 3 H), 1.31* (m, 3 H); $^{13}$C NMR (CDCl$_3$) δ 173.5*, 163.8*, 150.8, 145.5*, 135.3, 132.8*, 130.9, 127.3*, 126.2*, 122.7*, 117.8*, 113.3*, 89.6*), 84.3*, 67.5*, 67.1, 52.6, 50.1, 20.8*, 12.3*; $^{31}$P NMR (CDCl$_3$) δ 3.11, 2.54; IR (KBr) ν 3415, 3222, 3072, 2952, 1691, 1475, 1245, 1085, 1035, 929 cm$^{-1}$; UV(MeOH) λ$_{max}$ 215, 267 nm; FAB MS m/z 578.0105 (C$_{20}$H$_{22}$BrClN$_3$O$_8$P+H$^+$); HPLC t$_R$ 18.63, 20.63 min.

5-[2-Bromophenylmethoxyalaninylphosphate]-2',3'-didehydro-3'deoxythymidine (DDE 605). Yield: 0.36 g (19%); mp: 45–46° C.; $^1$H NMR (CDCl$_3$) δ 9.55 (s, 1 H), 7.47 (m, 2 H), 7.24 (m, 2 H), 6.99 (m, 2 H), 6.29 (m, 1 H), 5.88 (m, 1 H), 5.00 (m, 1 H), 4.35 (m, 2 H), 4.02 (m, 2 H), 3.66 (s, 3 H), 1.80* (m, 3 H), 1.30* (m, 3 H); $^{13}$C NMR (CDCl$_3$) δ 173.6*, 163.8*, 150.8, 147.3*, 135.4 *, 133.0*, 128.5*, 127.2*, 126.1*, 121.3 *, 114.4*, 111.3*, 89.6*, 84.3*, 67.2*, 52.5, 50.1*, 29.6, 20.8*, 12.4; $^{31}$P NMR (CDCl$_3$) δ 2.98, 2.37; IR (KBr) ν 3432, 3072, 2954, 1685, 1475, 1245, 1089, 933 cm$^{-1}$; UV(MeOH) λ$_{max}$ 207, 267 nm; FAB MS m/z 544.0469 (C$_{20}$H$_{23}$BrN$_3$O$_8$P+H$^+$); HPLC t$_R$ 8.37, 9.23 min.

5'-[2-Chlorophenylmethoxyalaninylphosphate]-2',3'-didehydro-3'deoxythymidine (DDE 606). 2.10 g (47%); mp: 43–45° C.; $^1$H NMR (CDCl$_3$) δ 9.80 (s, 1 H), 7.39 (m, 1 H), 7.29 (m, 1 H), 7.20 (m, 1 H), 7.13 (m, 1 H), 7.01 (m, 1 H), 6.92 (m, 1 H), 6.24 (m, 1 H), 5.81 (m, 1 H), 4.94 (m, 1 H), 4.28 (m, 3 H), 3.96 (m, 1 H), 3.59* (m, 3 H), 1.72* (m, 3 H), 1.25* (m, 3 H); $^{13}$C NMR (CDCl$_3$) δ 173.5*, 163.8 *, 150.8, 145.9*, 135.3*, 132.7*, 130.0, 127.5*, 127.0*, 124.8*, 121.2*, 111.0*, 89.3*, 84.3*, 66.9, 52.3, 49.8*, 20.5, 12.1*, $^{31}$P NMR (CDCl$_3$) δ 3.23, 2.67; IR (KBr) ν 3209, 3070, 2952, 1691, 1481, 1245, 1035, 931 cm$^{-1}$; UV(MeOH) λ$_{max}$ 214, 215, 219, 267 nm; FAB MS m/z 500.1028 (C$_{20}$H$_{23}$ClN$_3$O$_8$P+H$^+$); HPLC t$_R$ 7.62, 8.32 min.

5'-[2,5-Dichlorophenylmethoxyalaninylphosphate]-2',3'-didehydro-3'deoxythymidine (DDE 608). Yield: 0.68 g (30%); mp: 42–44° C; $^1$H NMR (CDCl$_3$) δ 9.43 (s, 1 H), 7.45 (m, 1 H), 7.25 (m, 2 H), 7.04 (m, 1 H), 6.99 (m, 1 H), 6.32 (m, 1 H), 5.88 (m, 1 H), 4.99 (m, 1 H), 4.32 (m, 3 H), 4.00 (m, 1 H), 3.67 (s, 3 H), 1.77* (m, 3 H), 1.33* (m, 3 H); $^{13}$C NMR (CDCl$_3$) δ 173.5*, 163.8, 150.8, 146.4*, 135.3, 132.7*, 130.7, 127.4, 125.8, 123.7*, 121.7*, 111.2*, 89.6*, 84.3*, 67.1*, 52.6, 50.1, 29.6, 20.7*, 12.3*; $^{31}$P NMR (CDCl$_3$) δ 3.24, 2.60; IR (KBr) ν 3423, 3205, 3072, 2954, 1691, 1475, 1245, 1093, 946 cm$^{-1}$; UV(MeOH) λ$_{max}$ 211, 216, 220, 268 nm; FAB MS m/z 534.0581 (C$_{20}$H$_{22}$Cl$_2$N$_3$O$_8$P+H+); HPLC t$_R$ 13.18 min.

The anti-HIV activity of the compounds was examined by evaluating their ability to inhibit HIV replication in peripheral blood mononuclear cells using previously described procedures (Uckun et al., 1998, *Antimicrobial Agents and Chem.*, 42(2):383–388). Percent inhibition of viral replication was calculated by comparing the p24 antigen levels from the test substance-treated infected cells with those from vehicle-treated infected cells.

All compounds (see Table 5) with a mono-halo substitution at the para position, including the previously described compound 113 with a 4-Br substitution, compound 604 with a 4-F substitution, and compound 609 with a 4-Cl substitution as well as compound 601 substituted with the electron drawing CN group at the para position, and compounds 603 and 608 with double halo substitutions had an IC$_{50}$ value of only 1 nM. Compounds with mono-halo substitutions at the 2- or 3-positions were less active (Mean IC$_{50}$=2.3±0.3) than compounds with mono-halo substitutions at the 4-position (Mean IC$_{50}$=1.0±0.0 nM, P<0.001). Compounds substituted with electron donating groups, including compounds 598, 599, and 600, also appeared to be less active than compounds with mono-halo substitutions at the 4-position (mean IC$_{50}$=11.7±6.7 nM, P=0.017). Thus, the presence of electron withdrawing groups seems to enhance the anti-HIV activity of this group of nucleoside analogs.

Next, it was determined if the anti-HIV potency of the aryl phosphate derivatives of stavudine could be predicted from their lipophilicity or hydrolysis rates. Contrary to the hypothesis of Siddiqui et al (Siddiqui et al., 1999, *J. of Med. Chem.*, 42:4122–4128), the lipophilicity of the aryl phosphate derivatives of stavudine did not correlate with their biologic activity against HIV-1 (R$^2$=0.06, t=0.86, P=0.4). Compounds with similar or identical partition coefficients had a wide range of IC$_{50}$ values (Table 1). For example, compounds 600 and 607 had the same partition coefficient as compound 508. Yet, their IC$_{50}$ values were 50% higher (6 nM vs. 4 nM) and 50% lower (2 nM vs. 4 nM), respectively, than the IC$_{50}$ value of compound 598. Whereas 2-Br, 2-Cl, and N(CH$_3$)$_2$ substitutions in the phenyl ring resulted in increased lipophilicity, as reflected by 2–2.5-fold higher partition coefficients, they did not increase the anti-HIV potency and in the case of 3-N(CH$_3$)$_2$ substitution caused a >10-fold loss in activity.

Figure 5:
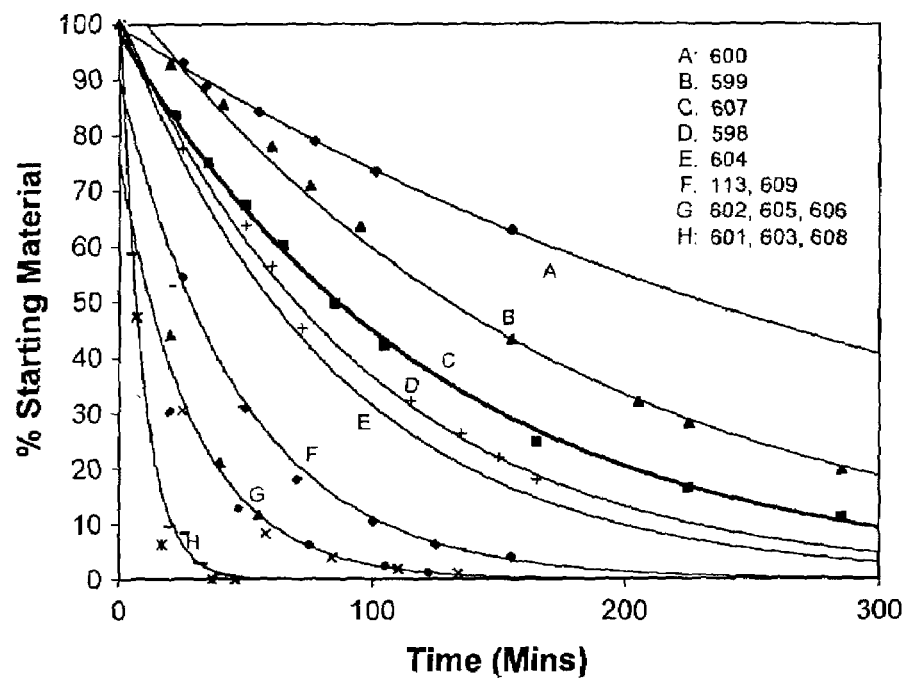
FIGS. 5A and 5B illustrate the effect of electron withdrawing groups on the rate of hydrolysis and potency of the compounds.
Figure 5:
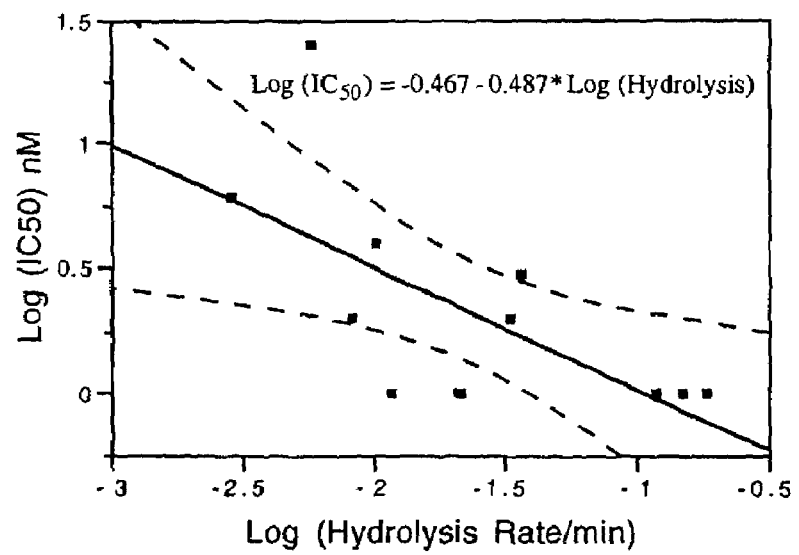

FIG. 1 depicts the literature proposed metabolic pathway of arylphosphate derivatives of d4T. The presence of electron withdrawing substituents at the para position of the phenyl moiety is likely to increase the hydrolysis rate of the phenoxy group in the metabolite precursor B generated by the carboxyesterase-dependent first step of the metabolic pathway of these aryl phosphate derivatives. In our earlier publication (Venkatachalam et al., 1998, *Bio. Med. Chem. Lett.*, 8:3121) we had postulated that the electronic effect induced by the electron withdrawing substituents would result in enhanced hydrolysis of the phenoxy group C yielding D and subsequently E, the precursors of the key metabolite Ala-d4T-MP. Chemical hydrolysis using alkaline conditions showed an increase in the amount of Ala-d4T-MP formation when electron withdrawing groups were present in the structure of these phosphoramidate derivatives (Venkatachalam et al., 1998, *Bio. Med. Chem. Lett.*, 8:3121). Because of its enhanced susceptibility to hydrolysis yielding substantially greater amounts of A-d4T-MP (the key precursor of the active d4T-TP metabolite), compounds containing electron withdrawing groups in their structure were postulated to be a more potent anti-HIV agents than compounds without such substitutions. This hypothesis is strongly supported by the experimental data presented in Table 6 and FIG. 5. Addition of electron withdrawing groups increased the rate of hydrolysis (FIG. 5A) and potency of the compound (FIG. 5B). The three compounds with electron donating substitutions (viz., 3-N(CH$_3$)$_2$, di-OMe and 4-OMe), had the slowest rates of hydrolysis and were the least potent. There was an inverse linear relationship between log 10 transformed values for the rate of hydrolysis and the IC$_{50}$ values (R$^2$=0.42, t=−2.8, P=0.017).

TABLE 5

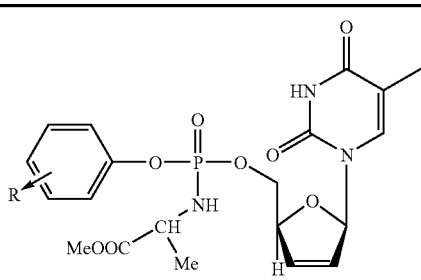

| DDE # | Substituents (R) | Partition Coefficient (log P) | Hydrolysis Rate (min$^{-1}$) | Solubility (mg/ml) |
|---|---|---|---|---|
| 113 | 4-Br | 1.21 | 0.0210 | 3.0 |
| 598 | 4-OMe | 0.39 | 0.0102 | 11.9 |
| 599 | 3-N(CH$_3$)$_2$ | 0.76 | 0.0058 | 18.0 |
| 600 | 2-diOMe | 0.40 | 0.0029 | 43.6 |
| 601 | 4-CN | 0.05* | 0.1199 | 4.0 |
| 602 | 3-Br | 1.12 | 0.0338 | 5.7 |
| 603 | 4-Br, 2-Cl | 1.81 | 0.1500 | 1.8 |
| 604 | 4-F | 0.54 | 0.0117 | 7.5 |
| 605 | 2-Br | 0.95 | 0.0336 | 4.2 |
| 606 | 2-Cl | 0.84 | 0.0370 | 44.7 |
| 607 | H | 0.38 | 0.0082 | |
| 608 | 2,5-diCl | 1.41 | 0.1840 | 3.7 |
| 609 | 4-Cl | 0.64 | 0.0216 | 1.4 |

Three physiochemical properties; Partition coefficient (Octanol/water), alkali hydrolysis rate, and biological activity are shown for each of the d4T derivatives.
*the value from 4-CN substituent is inaccurate because clear separation was not obtained between octanol and water.

Example 11

Activity of D4-T Derivatives Against Various HIV Strains

This example examined the antiviral activity of stavudine and 13 phenyl phosphoramidate derivatives of stavudine against the HTLVIII$_B$, RTMDR, A17 and A17V strains of HIV-1. (Table 6)

TABLE 6

|  |  | IC$_{50}$ (nM) | | | |
|---|---|---|---|---|---|
| Cmpd# | X | HTLVIII$_B$ | A17 | A17V | RTMDR |
| 113 | 4-Br | 1 ± 0 | 36 ± 21 | 47 ± 27 | 21 ± 12 |
| 598 | 4-OMe | 4 ± 2 | 121 ± 70 | 4 ± 2 | 1014 ± 586 |
| 599 | 3-N(Me)$_2$ | 25 ± 16 | 70 ± 49 | 11 ± 6 | 273 ± 158 |
| 600 | 2,6-OMe | 6 ± 3 | 137 ± 79 | 1 ± 1 | 1104 ± 637 |
| 601 | 4-CN | 1 ± 0 | 232 ± 134 | 20 ± 12 | 1636 ± 945 |
| 602 | 3-Br | 2 ± 2 | 42 ± 24 | 2 ± 1 | 493 ± 285 |
| 603 | 4-Br, 2-Cl | 1 ± 1 | 31 ± 18 | 6 ± 3 | 234 ± 135 |
| 604 | 4-F | 1 ± 0 | 91 ± 52 | 7 ± 4 | 218 ± 126 |
| 605 | 2-Br | 2 ± 0.7 | 42 ± 24 | 10 ± 6 | 523 ± 302 |
| 606 | 2-Cl | 3 ± 1 | 34 ± 20 | 15 ± 8 | 187 ± 108 |
| 607 | H | 2 ± 0.6 | 36 ± 21 | 6 ± 3 | 534 ± 308 |
| 608 | 2,5-diCl | 1 ± 0 | 37 ± 22 | 24 ± 14 | 22 ± 15 |
| 609 | 4-Cl | 1 ± 0.3 | 79 ± 46 | 22 ± 13 | 62 ± 43 |
| d4T | — | 18 ± 2 | — | — | — |
| AZT | — | 4 ± 1 | 0.055 | 0.005 | 68.0 |

All compounds synthesized showed satisfactory analytical data confirming their structures.

Stavudine (d4T) inhibited HTLVIIIB with an average IC$_{50}$ value of 18 nM. Twelve of the 13 derivatives of stavudine were substantially more potent than stavudine and inhibited HTLVIII$_B$ at nanomolar concentrations.

Similarly all compounds exhibited potent activity against the NNRTI resistant A17 and A17-variant strains of HIV-1 with nanomolar IC$_{50}$ values. Compounds 113, 608 and 609 were found to be most potent against the NRTI-resistant as well as NNRTI-resistant HIV-1 strain RTMDR with IC$_{50}$ values range from 20 to 60 nM.

Figure 6:
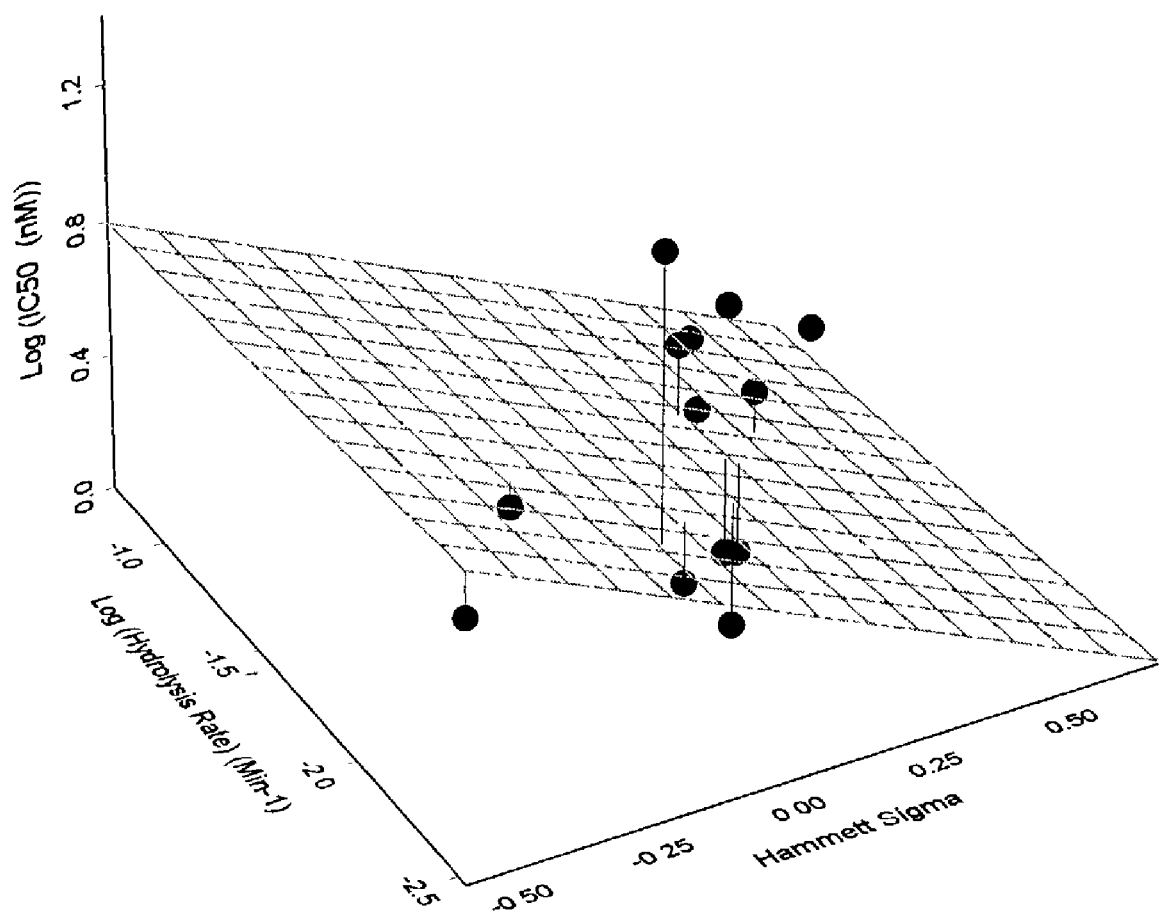
FIG. 6 depicts the correlation of the Hammet Sigma and hydrolysis rate values to IC50 values for inhibition of A17 replication. The solid circles represent compounds. The solid drop line represents deviation of the data points from the plane. The plane represents the multiple regression fit of Hammett Sigma and Hydrolysis rate to Log $IC_{50}$ values for inhibition of A17 replication.

The anti-HIV activity of the synthesized compounds against HTLVIIIB and A17 correlated with their susceptibility to alkaline hydrolysis as well as Hammett sigma values. (FIG. 6). The anti-HIV activity against RTMDR also correlated with the Hammett sigma values (Table 7). Inhibition of viral replication (IC$_{50}$ values) for each strain was correlated with each of the two physiochemical parameters; Hammetts Sigma, Hydrolysis rate, using non-parametric regression analysis (Spearman Rank). The Spearman Rho value was computed on ranked data to measure the strength of the correlation.

TABLE 7

|  |  | Virus Strain (regression of IC50 vs. Parameter) | | | | |
|---|---|---|---|---|---|---|
| Parameter | Statistic | HTLV$_{IIIB}$ | A17 | RTMDR | A17V | ADV |
| Hammett Sigma | Spearman Rho | −0.7 | −0.63 | −0.61 | 0.37 | −0.51 |
|  | p-value | 0.012 | 0.029 | 0.036 | 0.215 | 0.091 |
| Hydrolysis Rate | Spearman Rho | −0.58 | −0.61 | −0.57 | 0.34 | −0.47 |
|  | p-value | 0.049 | 0.036 | 0.055 | 0.276 | 0.125 |

In summary, we have synthesized aryl phosphoramidate derivatives of stavudine and examined their activity against various viral strains. Our data establishes that phosphoramidate derivatives having halo substitutions on phenyl ring have potent antiviral activity against resistant strains of HIV-1.

Example 12

Activity of D4-T Derivatives Against Clinical Isolates of Various HIV Strains

The purpose of the present study was to evaluate the antiretroviral activity of D4-T derivatives against primary clinical HIV-1 isolates.

Anti-HIV Drugs. The synthetic procedures for preparation of compound 113, STV-5'[para-bromophenyl methoxyalanininyl phosphate], have been previously described. Zidovudine(ZDV)/AZT (GlaxoWellcome), lamivudine (LMV)/3TC/Epivir (GlaxoWellcome), stavudine (STV)/d4T/Zerit (Bristol-Myers Squibb Co), Nelfinavir (NLV)/Viracept (Agouran), and Nevirapine (NVP) (Boehringer Ingelheim/Roxane) were obtained from the Parker Hughes Institute Investigational Pharmacy Department.

Viruses. 20 primary clinical isolates with genotypic and/or phenotypic NRTI-resistance (isolated in the laboratory of D. Richman) and 10 clinical isolates with phenotypic stavudine resistance (obtained through the AIDS Research and Reference Reagent Program, NIAID) were used in the current study. The HIV-1 strains HTLVIIIB (wildtype RT, NRTI-sensitive, NNRTI-sensitive), A17 (Y181C mutant, NNRTI-resistant), A17-variant (Y181C+K103N mutant, NNRTI-resistant), and RT-MDR (M41L, V106N, T215Y; NRTI-resistant, NNRTI-resistant) were also obtained from the AIDS Research and Reference Reagent Program, NIAID.

Antiviral susceptibility assays. Phenotypic drug susceptibility studies of HIV-1 isolates and strains were performed by measuring the production of the p24 gag protein in peripheral blood mononuclear cells (PBMC) from seronegative healthy volunteers in the presence of increasing concentrations of the anti-HIV agent using the quantitative Coulter HIV-1 p24 antigen enzyme immunoassay (EIA) and HIV-1 p24 Antigen Kinetic Standard (Beckman Coulter), as previously described (Uckun, 1998, *Antimicrobial Agents and Chemotherapy* 37(4): 835–38). Informed consent was obtained from the blood donors according to DHHS guidelines using consent forms approved by the Institutional Review Board. In brief, PBMC were cultured for 72 h in RPMI 1640 medium (Gibco) supplemented with 20% (vol/vol) heat-inactivated fetal bovine serum, 5% human interleukin-2 (Zeptometrix), 2 mM L-glutamine, 25 mM HEPES, 2 g/L $NaHCO_3$, 100 U/ml penicillin/streptomycin (Gibco), 50 µg/ml gentamicin (Gibco), and 5 µg/ml phytohemagglutinin-P (PHA-P) (Sigma) for 24–72 hours prior to exposure to HIV at a multiplicity of infection of 0.001–0.1 during a 1-h adsorbtion period at 37±1° C. in a humidified 5–7% $CO_2$ atmosphere. Subsequently, cells were cultured in 96-well microtiter plates (100 µl/well; $2\times10^6$ cells/ml, triplicate wells) in the presence of the anti-HIV agents at 6–7 different concentrations ranging from 0.0001 µM to 100 µM, and 25 µL aliquots of culture supernatants were removed from the wells on day 6 after infection for p24 EIA, as previously described (Uckun, 1998, *Antimicrobial Agents and Chemotherapy*, 37(4):835–38). Controls included uninfected and untreated cells (background control) and infected but untreated (virus control) cells. The p24 EIA utilizes a murine monoclonal antibody to HIV core protein used to coat microwell strips to which the antigen present in the test culture supernatant samples binds. Percent inhibition of viral replication was calculated by comparing the p24 values from the test substance-treated infected cells with p24 values from untreated infected cells (i.e., virus controls). The $IC_{50}$ values were determined using the Statview statistics program (SAS Institute, Inc.). In parallel, the effects of various treatments on cell viability were also examined as previously described (Uckun, 1998, *Antimicrobial Agents and Chemotherapy*, 42:383–388). In brief, noninfected PBMC were treated with each compound for 5 days under identical experimental conditions. A microculture tetrazolium assay (MTA) was performed to quantitate cellular proliferation (Uckun, 1998, *Antimicrobial Agents and Chemotherapy*, 42:383–388). The cytotoxic concentrations which inhibit cellular proliferation by 50% ($CC_{50}$ values) were determined using the Statview statistics program (SAS Institute, Inc.).

Plaque Formation Assays. The syncytial focus (plaque) assay permits quantitation of infectivity of HIV. In brief, a CD4-expressing HeLa cell line (HT4–6C) (AIDS Research and Reference Reagent Program, NIAID) is cultured in 24-well tissue culture plates at $2.5–3.0\times10^4$ cells/ml in the presence of virus inoculum (100 plaque forming units) and several concentrations of the antiviral agent. The virus was added first for a 2 hr incubation time prior to addition of the antiviral agents. The cells were cultured for 3 days and cultures were assayed for syncytium formation by submerging the plates in 100% methanol for 15 min, staining with 0.3% crystal violet for 5 min, and counting the plaques in each well with an inverted microscope (Uckun, 1998, *Antimicrobial Agents and Chemotherapy*, 37(4):835–38). Percent inhibition of plaque formation was calculated by comparing the plaque numbers from the test substance-treated infected cells with the plaque numbers from untreated infected cells (i.e., virus controls). The $IC_{50}$ values were determined using the Statview statistics program (SAS Institute, Inc.).

Statistical analysis. Each drug (ZDV, compound 113, STV, 3TC, nevirapine, nelfinavir) was tested at 6–7 different concentrations ranging from 0.0001 µM to 100 µM. Each assay was set up in triplicate wells and repeated 1–3 times. The $IC_{50}$, and $IC_{90}$ values were calculated from each set of triplicate wells using nonlinear regression modeling of the exponential form of the linearized equation. For primary clinical HIV-1 isolates, the inhibition data were evaluated separately for STV-resistant and ZDV-resistant isolates. The inhibition constants were $log_{10}$ transformed to homogenize the variances within each group. Paired t-tests were performed in order to test for differences between means of $IC_{50}/IC_{90}$ values for compound 113 and STV or ZDV. P-values below 0.05 were deemed significant (JMP Software, SAS)

Phenotypic drug susceptibility studies of HIV-1 isolates and strains were performed by measuring the production of the p24 gag protein in peripheral blood mononuclear cells (PBMC) from seronegative healthy volunteers in the presence of increasing concentrations of the anti-HIV agent using the quantitative Coulter HIV-1 p24 antigen enzyme immunoassay (EIA) and HIV-1 p24 Antigen Kinetic Standard (Beckman Coulter), as previously described. StatView was used in the calculation of the $IC_{50}$ values from each set of triplicate wells using the linearized form of an exponential equation (InY=Inb0+b1X; where Y=% inhibition, X=drug concentration). The inhibition constants were $log_{10}$ transformed to homogenize the variances within each group. Paired t-tests were performed in order to test for differences between means of $IC_{50}$ values for Compound 113 and STV or ZDV across each viral strain. P-values below 0.05 were deemed significant (JMP Software, SAS).

The anti-HIV activity of compound 113 in side by side comparison with stavudine and zidovudine against 10 zidovudine-sensitive clinical HIV-1 isolates was examined by evaluating its effects on HIV-1 p24 antigen production in human PBMC infected with one of these isolates. Nine of these isolates originating from South America, Asia, and sub-Saharan Africa had a non-B envelope subtype (A=2, C=2, F=3, G=2, Table 8). The $IC_{50}$ and $IC_{90}$ of stavudine against these isolates ranged from 0.1 µM to 0.8 µM (mean±SE=0.24±0.07 µM) and from 1.0 µM to 40.9 µM (mean±SE=6.38±3.89 µM), respectively. By comparison, the $IC_{50}$ and $IC_{90}$ of zidovudine against these isolates ranged from 0.001 µM to 0.01 µM (mean±SE=0.004±0.001 ΞM) and from 0.011 µM to 0.09 µM (mean±SE=0.05±0.01 µM), respectively. In contrast, the $IC_{50}$ and $IC_{90}$ values for compound 113 were 0.002±0.001 µM and 0.03±0.01 ΞM, respectively. Thus, as shown in Table 8, compound 113 was more potent than stavudine (P<0.0001; paired t-test) or zidovudine (P=0.04 for $IC_{50}$ values and P=0.03 for $IC_{90}$ values; paired t-test) against these clinical isolates. Notably, phenotypically stavudine-resistant HIV-1 isolates, such as BR/92/25 and BR/93/29, were exquisitely sensitive to compound 113 (Table 8).

>100,000. Similarly, the average $CC_{50}$ value of zidovudine was 95.6±2.9 µM with a corresponding selectivity index (SI=$CC_{50}$/$IC_{50}$) of 31,867. By comparison, the average $CC_{50}$ value for stavudine was 4.5±1.7 µM with a corresponding SI value of only 196 and the average $CC_{50}$ value for lamivudine was 55±45 µM with a corresponding SI value of only 1375. Thus, compound 113 had a better selectivity index than zidovudine, stavudine, or lamivudine.

The in vitro anti-HIV activity of compound 113 against the NRTI-sensitive laboratory strain $HTLV_{IIIB}$ was then evaluated in 17 independent experiments, each performed in triplicate. The testing was performed in side by side comparison with stavudine in 8 experiments and zidovudine in 13 experiments, lamivudine in 3 experiments, nelfinavir in 6 experiments, and nevirapine in 6 experiments (Table 9). Compound 113 exhibited potent anti-HIV activity with nanomolar $IC_{90}$ values and it was consistently and significantly more effective than the NRTI zidovudine, stavudine or lamivudine: The mean $IC_{50}$ and $IC_{90}$ values of compound 113 were 0.001±0.000 µM and 0.052±0.024 µM respec-

TABLE 8

Activity of compound 113 Against Zidovudine-Sensitive Primary Clinical HIV-1 Isolates[a]

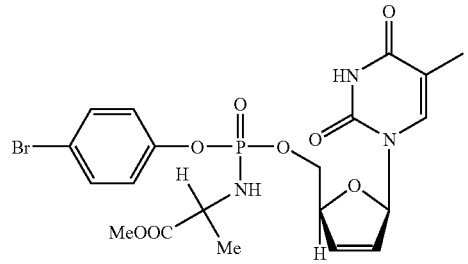

| | | | | IC$_{50}$, µM (p24)[b] | | |
|---|---|---|---|---|---|---|
| HIV-1 Isolate[a] | Catalog# | HIV-1 subtype | Origin | Cmpd 113 | STV | ZDV |
| 92RW016 | 2061 | A/A | Rawanda | 0.003 | 0.1 | 0.003 |
| 92RW008 | 1746 | —/A | Rawanda | 0.0008 | 0.2 | 0.002 |
| 92BR003 | 1751 | B/B | Brazil | 0.0006 | 0.1 | ND |
| 92BR025 | 1777 | C/C | Brazil | 0.001 | 0.4 | 0.004 |
| 93IN101 | 2900 | —/C | India | 0.0005 | 0.1 | 0.001 |
| 93BR019 | 2314 | —/BF | Brazil | 0.0008 | 0.2 | 0.002 |
| 93BR020 | 2329 | F/F | Brazil | 0.007 | 0.2 | 0.002 |
| 93BR029 | 2338 | F/B | Brazil | 0.0008 | 0.8 | 0.007 |
| HIV-1$_{JV1083}$ | 3191 | —/G | Nigeria | 0.001 | 0.2 | 0.003 |
| HIV-1$_{G3}$ | 3187 | —/G | Nigeria | 0.0005 | 0.1 | 0.01 |
| | | | Mean ± SE | 0.002 ± 0.001 | 0.24 ± 0.07 | 0.004 ± 0.001 |
| | | | | | (P = 0.0001) | (P < 0.04) |

[a]The primary HIV-1 isolates were obtained through the NIH AIDS Research and Reference Reagent Program: and their catalog numbers are indicated in the table. HIV-1 subtype: gag/env
[b]The drug susceptibility assays were performed using PBMC, as described in Materials and Methods. Results are expressed as the average $IC_{50}$ values from 2 independent experiments. STV, stavudine; ZDV, zidovudine; compound 113.
ND, not determined.

The laboratory strains were obtained through the NIH AIDS Research and Reference Reagent Program. All primary HIV-1 isolates were recovered from peripheral blood leukocytes of HIV-infected individuals who had been treated with NRTI using previously described culture techniques. The drug susceptibility assays were performed using PBMC or MT-2 cells (RT-MDR only), as described in Materials and Methods. The $CC_{50}$ values were >100 µM for both nevirapine and compound 113 (data not shown).

In 7 of these 17 experiments, we examined the cytotoxicity of compound 113 against PBMC. In each of the 7 experiments, the $CC_{50}$ values were >100 µM. Thus, the selectivity index (SI=$CC_{50}$/$IC_{50}$) of compound 113 was tively. By comparison, the mean $IC_{50}$ and $IC_{90}$ values of stavudine were 0.023±0.008 µM and 1.470±0.614 µM, respectively (P<0.001, Table 9). Similarly, the mean $IC_{50}$ and $IC_{90}$ values of lamivudine were substantially (P<0.001) higher than those of compound 113 (0.040±0.025 µM and 1.824±0.747 µM, respectively; Table 9). Compound 113 also had better $IC_{50}$ and $IC_{90}$ values when compared to zidovudine ($IC_{50}$:0.001±0.000 vs 0.003±0.001, P<0.001; $IC_{90}$: 0.045±0.028 vs 0.093±0.034, P<0.05). Furthermore, compound 113 was more effective than the NNRTI nelfinavir or nevirapine in each of the 6 independent experiments (Table 9).

TABLE 9

Activity of Compound 113 Against HTLV$_{IIIB}$ in Human PBMC Anti-HIV Activity and Selectivity Parameters

| Drug | IC$_{50}$, μM | IC$_{90}$, μM | CC$_{50}$, μM | SI(CC$_{50}$/IC$_{50}$) |
|---|---|---|---|---|
| Cmpd 113 (n = 17) | 0.001 ± 0.000 | 0.052 ± 0.024 | >100 | >100,000 |
| STV (n = 8) | 0.023 ± 0.008 | 1.470 ± 0.614 | 4.5 ± 1.7 | 196 |
| ZDV (n = 13) | 0.003 ± 0.001 | 0.093 ± 0.034 | 95.6 ± 2.9 | 31,867 |
| LMV (n = 3) | 0.040 ± 0.025 | 1.824 ± 0.747 | 55 ± 45 | 1,375 |
| NVP (n = 6) | 0.024 ± 0.007 | 1.095 ± 0.478 | 5.1 ± 2.3 | 213 |
| NFV (n = 6) | 0.006 ± 0.003 | 0.084 ± 0.038 | 3.5 ± 1.4 | 583 |

IC$_{50}$: concentration at which the drug inhibits p24 production in HTLV$_{IIIB}$-infected PBMC by 50%.
IC$_{90}$: concentration at which the drug inhibits p24 production in HTLV$_{IIIB}$-infected PBMC by 90%.
CC$_{50}$: cytotoxic concentration at which the drug reduces the viability of PBMC by 50%.
SI: selectivity index. compound 113, Comopund 113; STV, stavudine; ZDV, zidovudine; LMV, lamivudine; NVP, nevirapine; NFV, nelfinavir.

We next examined the anti-HIV activity of compound 113 against 20 genotypically and/or phenotypically zidovudine-resistant primary clinical HIV-1 isolates (Table 10). The IC$_{50}$ of zidovudine against 11 of these 20 isolates was >1 μM and the IC$_{50}$ values for the remaining 9 isolates were >0.1 μM (mean±SE=1.6±0.5 μM). Nineteen isolates were genotyped and each was found to have 2–5 TAMs associated with NRTI-resistance. L74V mutation conferring didanosine resistance was found in one isolate (X267-1) and the multidrug resistance mutation F116Y was found in one isolate (X267-5). As shown in Table 10, compound 113 was active against each of these isolates at nanomolar concentrations regardless of the degree of their phenotypic or genotypic zidovudine resistance with an average IC$_{50}$ value of 8.7±2.8 nM (range: <1 nM to 42 nM). Notably, the phenotypically highly zidovudine-resistant G190-6 and G704-2 isolates carrying 5 TAMs were inhibited by Compound 113 with IC$_{50}$ values of 2.8 nM and 3.2 nM, respectively. The superiority of compound 113 over zidovudine against zidovudine-resistant isolates was statistically significant (P<0.0001, paired t-test; Table 10). Thus, phenotypic or genotypic zidovudine resistance is not associated with compound 113 resistance.

TABLE 10

| HIV-1[b] | | IC$_{50}$, μM[a] | |
|---|---|---|---|
| Isolate | RT Gene Mutation | ZDV | compound 113 |
| RT-MDR(Con) | M41L, L74V, T215Y, V106N | >10 | <0.001 |
| G910-6 | M41L, D67N, K70R, T215Y, K219Q | >3.2 | 0.0028 |
| T156-3 | M41L, E44D, D67N, T69D, L210W, T215Y | >3.2 | 0.0033 |
| G890-1 | K20R, M41L, D67N, T69N, K70R, L210W, T215Y | >3.2 | 0.006 |
| G780-1 | M41L, D67N, K70R, T215F, K219Q | >3.2 | 0.035 |
| C467-4 | K20R, D67N, K70R, Y188L, T215F, K219Q | 3.2 | 0.042 |
| G691.2 | N.D. | 2.6 | 0.005 |
| G704-2 | M41L, D67N, K70R, L210W, T215Y | 1.8 | 0.0032 |
| P798-1 | M41L, T215Y | 1.8 | 0.0075 |
| Q252-2 | M41L, L210W, T215Y | 1.7 | 0.0019 |
| Y270-7 | M41W, Y188L, T215N | 1.5 | 0.009 |
| S762-4 | M41L, T215Y | 1.2 | 0.008 |
| X165-8 | D67N, T69N, K70R, K103N, Y181C, T215F, K219E | 0.9 | 0.013 |
| X165-9 | K20R, D67N, K103N, T215Y | 0.9 | 0.002 |
| S159-2 | M41L, K103N, T215Y | 0.7 | 0.00078 |
| X267-5 | M41L, F116S, T215Y | 0.6 | 0.03 |
| X267-1 | M41L, L74V, L210W, T215Y | 0.6 | 0.00015 |
| X267-2 | M41L, T215Y | 0.4 | 0.00018 |
| R416-10 | M41L, T215Y | 0.3 | 0.0002 |
| 92BR019 | D67N, L214F, T215D, K219Q | 0.2 | 0.002 |
| C140 | M41L, M184V, T215Y | 0.1 | 0.0025 |
| | Mean ± SE: [P < 0.0001, paired t-test] | 1.6 ± 0.3 | 0.0087 ± 0.0027 |

[a]The results presented were obtained from a representative antiviral assay. The standard error between individual antiviral assays was <10% of the average IC$_{50}$.
[b]All primary HIV-1 isolates except for 92BR019 were recovered from peripheral blood leukocytes of HIV-infected individuals who had been treated with NRTI using previously described culture techniques (33–35). RT-MDR is a NRT-resistant and NNRTI-resistant laboratory strain of HIV-1, which was included as a control. HIV-1 RT-MDR-1/MT-2 (Catalog#252) and 92BR019 (Catalog#1778; Envelope subtype B) were obtained through the NIH AIDSResearch and Reference Reagent Program. The drug susceptibility assays were performed using PBMC, as described in Materials and Methods. ZDV, zidovudine; compound 113, Comopund 113

Notably, the phenotypically highly zidovudine-resistant G190-6 and G704-2 isolates (zidovudine $IC_{50}$ value >10 µM) carrying 5 TAMs were inhibited by compound 113 with average $IC_{50}$ values of 2.8 nM and 3.2 nM, respectively. These findings provide evidence that compound 113 is a highly potent inhibitor of primary clinical HIV-1 isolates with a genotypic and/or phenotypic NRTI-resistant profile. The documented in vitro potency of compound 113 against primary clinical HIV-1 isolates with genotypic and/or phenotypic NRTI-resistance as well as non-B envelope subtype together with favorable toxicity profile in rodent and non-rodent animal species and its in vivo antiretroviral activity in HIV-infected Hu-PBL SCID mice as well as FIV-infected cats warrants the further development of this promising new NRTI compound.

We also examined the antiviral activity of compound 113 against 9 different zidovudine-resistant primary clinical HIV-1 isolates in syncytial focus (plaque) formation assays using the CD4-expressing HeLa cell line HT4–6C. As shown in Table 11, compound 113 inhibited the infectivity of each isolate in a concentration-dependent fashion with nanomolar $IC_{50}$ values with a mean $IC_{50}$ value of 79.4±18.7 nM which was significantly lower than the $IC_{50}$ value of 3.9±1.0 µM for zidovudine against the same isolates (P<0.0001, paired t-test on $\log_{10}$-transformed values).

primary clinical HIV-1 isolates was 11.2±6.5 nM. These clinical HIV-1 isolates also harbor additional RT gene mutations conferring NRTI-resistance and display a zidovudine-resistant phenotype (see Table 9 and Table 10). Similarly, compound 113 inhibited the replication of the multidrug-resistant, V106N mutant HIV-1 strain RT-MDR also harboring the NRTI-resistance associated RT mutations M41L and T215Y in the human T-cell line MT2 with subnanomolar $IC_{50}$ values without any evidence of cytotoxicity even at a 100 µM concentration (Table 12).

TABLE 12

Activity of compound 113 Against NNRTI-Resistant HIV

| HIV-1 Strain or Isolate | NNRTI Binding Pocket Mutation | $IC_{50}$, µM Nevirapine | compound 113 |
|---|---|---|---|
| Laboraory Strains | | | |
| A17 | Y181C | 47 ± 7(n = 38) | <0.001(n = 3) |
| A17-Var | Y181C, K103N | 32 ± 7(n = 38) | <0.001(n = 5) |
| RT-MDR | V106N | 18 ± 8(n = 21) | <0.001(n = 5) |

TABLE 11

Compound 113 Reduces Infectivity of ZDV-Resistant Primary Clinical HIV-1 Isolates in Syncytial Focus Formation Assays[a]

| | | $IC_{50}$, µM(Plaque Assay)[b] | |
|---|---|---|---|
| HIV-1 Isolate | RT Mutation | ZDV | Compound 113 |
| G691.2 | N.D. | 7.8 | 0.06 |
| G190-6 | M41L, D67N, K70R, T215Y, K219Q | 10.0 | 0.10 |
| G704-2 | M41L, D67N, K70R, L210W, T215Y | 5.7 | 0.08 |
| G890-1 | K20R, M41L, D67N, T69N, K70R, L210W, T215Y | 3.6 | 0.04 |
| G780-1 | M41L, D67N, K70R, T215F, K219Q | 1.8 | 0.015 |
| J179-1 | M41L, D67N, L210W, T215Y | 2.6 | 0.18 |
| U317-8 | M41L, L210W, T215Y | 2.0 | 0.03 |
| M709-1 | L1210W, T215Y | 3.0 | 0.08 |
| Q252-2 | M41L, L210W, T215Y | 2.8 | 0.11 |
| | Mean ± SE | 3.9 ± 1.0 | 0.0794 ± 0.0187 |
| | [P < 0.0001, paired t-test] | | |
| H112-2 | None (ZDV-sensitive control | 0.015 | 0.015 |

[a]Syncytial focus (plaque) formation assays were performed using the CD4-positive HeLa cell line HT4-6C (AIDS Research and Reference Reagent Program, NIAID), as described in Materials and Methods.
[b]The $IC_{50}$ values were calculated using the median effect equation by comparing the plaque numbers from the test substance-treated cultures with plaque numbers from untreated cultures (i.e.., virus controls) (33). P-values were calculated using paired t-tests on $\log_{10}$-transformed $IC_{50}$ values.

Dozens of mutant strains have been characterized as resistant to NNRTI compounds, including L1001, K103N, V106A, E138K, Y181C and Y188H/L. In particular, the Y181C and K103N mutants may be the most difficult to treat, because they are resistant to most of the NNRTIs compounds that have been examined. Therefore, we next examined the ability of compound 113 to inhibit the replication of HIV-1 strains/isolates with Y181C, K103N, V106A, or Y188L mutations in human peripheral blood mononuclear cells, as measured by production of the p24 gag protein compound 113 inhibited the replication of the Y181C mutant HIV-1 strain A17, the Y188L mutant primary clinical HIV-1 isolates C467-4 and Y270-7, the K103N mutant primary clinical HIV-1 isolates X-165-9 and S-159-2, the Y181C+K103N double mutant HIV-1 strain A17-variant, the Y181C+K103N double mutant primary clinical isolate X-165–8 in human peripheral blood mononuclear cells with subnanomolar to nanomolar $IC_{50}$ values (Table 11). The average $IC_{50}$ value of compound 113 against the TABLE 12-continued Activity of compound 113 Against NNRTI-Resistant HIV

| HIV-1 Strain or Isolate | NNRTI Binding Pocket Mutation | $IC_{50}$, µM Nevirapine | compound 113 |
|---|---|---|---|
| Primary Isolates | | | |
| RW/92/8 | V179I | 0.1 | 0.0008 |
| C467-4 | Y188L | N.D | 0.042 |
| Y270-7 | Y188L | N.D. | 0.009 |
| X165-8 | K103N, Y181C | N.D | 0.013 |
| X165-9 | K103N | N.D | 0.002 |
| S159-2 | K103N | N.D | <0.0001 |
| | Mean ± SE | ND | 0.0112 ± 0.0065 |

Many of the TAMs observed in the zidovudine-resistant isolates, such as M41L, D67N, K70R, and M184V, involve residues within a 10 Å distance from the catalytic site on the palm and fingers domains near the catalytic site and would likely impair the inhibitor binding and/or the dynamic process of inhibitor incorporation. Remarkably, compound 113 was capable of inhibiting each of these isolates at nanomolar concentrations even though some of the mutations were within a 3–10 Å from the stavudine-triphosphate binding site. Finally, unlike nucleoside analogs, NNRTI bind to an allosteric site of HIV-1 RT, which is approximately 10–20 Å away from the catalytic site. NNRTI binding induces rotamer conformation changes in some residues (Y181 and Y188) and renders the thumb region more rigid. Both events consequently would alter the substrate binding mode and/or affect the translocation of the double strand, which are probably critical for the polymerase function of RT, thereby leading to a noncompetitive inhibition of the enzyme. Nucleoside analogs like compound 113 theoretically should not be sensitive to the mutations in the NNRTI binding pocket. In accordance with our expectations, compound 113 inhibited HIV-1 isolates with NNRTI binding pocket mutations at nanomolar concentrations.

All publications, patents, and patent documents described herein are incorporated by reference as if fully set forth. The invention described herein can be modified to include alternative embodiments. All such obvious alternatives are within the spirit and scope of the invention, as claimed below. While a detailed description of the present invention has been provided above, the invention is not limited thereto. The invention described herein may be modified to include alternative embodiments, as will be apparent to those skilled in the art. All such alternatives should be considered within the spirit and scope of the invention, as claimed below.

I claim:

1. A method of inhibiting virus replication in a cell infected with a resistant stain of HIV comprising administering to the infected cell a virus replication inhibiting amount of a compound of Formula I

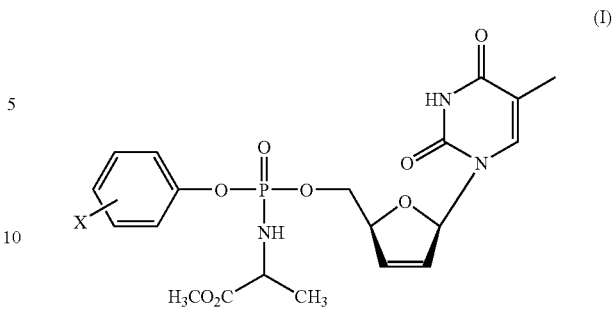

wherein X is an electron withdrawing group, or a pharmaceutically acceptable salt thereof.

2. The method of claim 1, wherein X is I, or $NO_2$.
3. The method of claim 1, wherein X is Cl.
4. The method of claim 1, wherein X is Br.
5. The method of claim 1, wherein the resistant strain of HIV is A17, or A17-V.
6. The method of claim 1, wherein the resistant HIV stain is a clinical isolate obtained from an infected individual who is not responding or has not responded to at least one treatment course.
7. The method of claim 6, wherein the HIV strain is a non-B subtype.
8. The method of claim 1, wherein said administering to an infected cell comprises administering to an animal.
9. The method of claim 8, wherein the animal is a human.
10. The method of claim 9, wherein the virus replication inhibiting amount is from about 1 to about 500 mg/kg body weight of the animal.
11. The method of claim 10, wherein the virus replication inhibiting amount is from about 10 to 100 mg/kg body weight of the animal.
12. The method of claim 1, wherein said isolate is infected with an HIV strain having a mutated reverse transcriptase, the mutation comprising one or more of: M41L, D67N, K70R, L74V, K103N, V106N/A, E138K, Y181C, Y188H/L, T215Y/F/D.
13. The Method of claim 1, wherein the resistant strain of HIV is resistant to stavudine.
14. The method of claim 13, wherein the resistant strain of HIV is resistant to zidovudine.
15. The nethod of claim 1, wherein the HIV strain is a non-B serotype.

* * * * *

UNITED STATES PATENT AND TRADEMARK OFFICE
CERTIFICATE OF CORRECTION

PATENT NO. : 7,144,874 B2
APPLICATION NO. : 10/281333
DATED : December 5, 2006
INVENTOR(S) : Uckun Page 1 of 1

It is certified that error appears in the above-identified patent and that said Letters Patent is hereby corrected as shown below:

Col. 2, line 10: "where X= =H" should read --where X=H--

Col. 2, line 11: "where X= =OCH₃" should read --where X=OCH₃--

Col. 2, line 12: "where X= =Br" should read --where X=Br--

Col. 17, line 35: "6.15-6.09 (m, 111H)," should read --6.15-6.09 (m, 1H),--

Col. 17, line 38: "156.3, 143.7*," should read --156.3, 150.3, 143.7*,--

Col. 18, line 21: "measured by RT activity," should read --measured by assays of RT activity,--

Col. 18, line 44: "phosopate derivatives" should read --phospate derivatives--

Col. 30, line 7: "were log, transformed" should read --were log₁₀ transformed--

Col. 37, line 10: "0.001 ΞM)" should read --0.001 µM)--

Col. 37, line 13: "0.01 ΞM," should read --0.01 µM,--

Col. 43, line 44, claim 1: "resistant stain of" should read --resistant strain of--

Col. 44, line 21, claim 6: "resistant HIV stain" should read --resistant HIV strain--

Col. 44, line 44, claim 15: "The nethod of claim" should read --The method of claim--

Signed and Sealed this

Twenty-fourth Day of July, 2007

JON W. DUDAS
*Director of the United States Patent and Trademark Office*